United States Patent [19]
Bugg et al.

[11] Patent Number: 6,027,565
[45] Date of Patent: Feb. 22, 2000

[54] METHOD AND APPARATUS FOR CRYSTALIZING MACROMOLECULES IN MICROGRAVITY

[76] Inventors: Charles E. Bugg, 4370 Cliff Rd., Birmingham, Ala. 35222; Lawrence L. Delucas, 2739 Altadena Rd., Birmingham, Ala. 35243; Tattanhalli L. Nagabhushan, 3 Sunset La., Parsippany, N.J. 07054; Paul P. Trotta, 2429 Harmon Cove Towers, Secaucus, N.J. 07094; Michael D. Harrington, 2438 Rockcreek Rd., Birmingham, Ala. 35226; John Bradford Bishop, deceased, late of Lindale, Ga.; by Sue C. Bishop, executrix, P.O. Box 412, Lindale, Ga. 30147

[21] Appl. No.: 08/947,596

[22] Filed: Oct. 9, 1997

Related U.S. Application Data

[63] Continuation-in-part of application No. 08/441,256, May 15, 1995, abandoned, which is a continuation of application No. 08/281,865, Jul. 28, 1994, abandoned, which is a continuation of application No. 08/076,948, Jun. 16, 1993, abandoned, which is a continuation of application No. 07/836,658, Feb. 18, 1992, abandoned, which is a continuation-in-part of application No. 07/659,948, Feb. 25, 1991, abandoned.

[51] Int. Cl.$^7$ .................................................. G30B 35/00
[52] U.S. Cl. ...................... 117/202; 117/206; 117/901; 117/927; 422/245.1
[58] Field of Search .................. 422/58, 101, 240, 422/245.1; 117/202, 203, 206, 223, 224, 901, 902, 925, 927

[56] References Cited

U.S. PATENT DOCUMENTS

| | | | |
|---|---|---|---|
| 4,672,218 | 6/1987 | Chrisman et al. | 250/574 |
| 4,738,831 | 4/1988 | Naumann et al. | 117/206 |
| 4,755,363 | 7/1988 | Fujita et al. | 117/206 |
| 4,886,646 | 12/1989 | Carter et al. | 117/202 |
| 4,919,899 | 4/1990 | Herrmann et al. | 422/245.1 |
| 5,009,861 | 4/1991 | Plaas-Link | 117/223 |
| 5,013,531 | 5/1991 | Snyder et al. | 117/223 |

OTHER PUBLICATIONS

McPherson (1976), Method. Bioichem. Analysis, 23, 249–345.
Cawuthers (1977), Journal Crystal Growth, 42, 379–385.
Littke, et al. (1984), Science, 203–204.
Smith, et al. (1996), "A novel complex of phenolic derivative with insulin: Structural features related to the T–R transition", Protein Science, 5, 1502–1511.
Long, et al. (1994), Microgravity Science and Technology, "Protein Crystal Growth in Microgravity—Temperature Induced Large Scale Crystallization of Insulin", VII/2, 196–202.
Long, et al. (1996), Journal of Crystal Growth, "Protein crystal growth in microgravity review of large scale temperature induction method: bovine insulin, human insulin and human alpha interferon", 168, 233–243.
Reichert, et al. (1996), American Institute of Physics, "Macroscale Production and Analysis of Crystalline Interferon Alpha–2B in Microgravity on STS–52", Conf. 960109, 139–148.
Nagabhushan, et al. (1995), American Institute of Physics, "Macroscale Production of Crystalline Interferon Alfa–2B in Microgravity on STS–52", Conf 950110, 183–191.

Primary Examiner—Benjamin Utech
Assistant Examiner—Donald L. Champagne
Attorney, Agent, or Firm—Merchant & Gould P.C.

[57] ABSTRACT

An apparatus for producing crystals of a macromolecule in microgravity includes a container 100 which is made of a material having a low thermal conductivity and an open end. A thermally conductive lid 102 is fitted on the open end of the container to close the container and a heat source/sink 114 is provided in thermal contact with the thermally conductive lid to generate a temperature gradient within the container. When a solution of the macromolecule is provided in the container, the temperature gradient induces and control the crystallization of the macromolecule. In operation, a temperature ramp from a start temperature to an end temperature is used to maintain and control the temperature gradient.

10 Claims, 27 Drawing Sheets

FIG. 18A
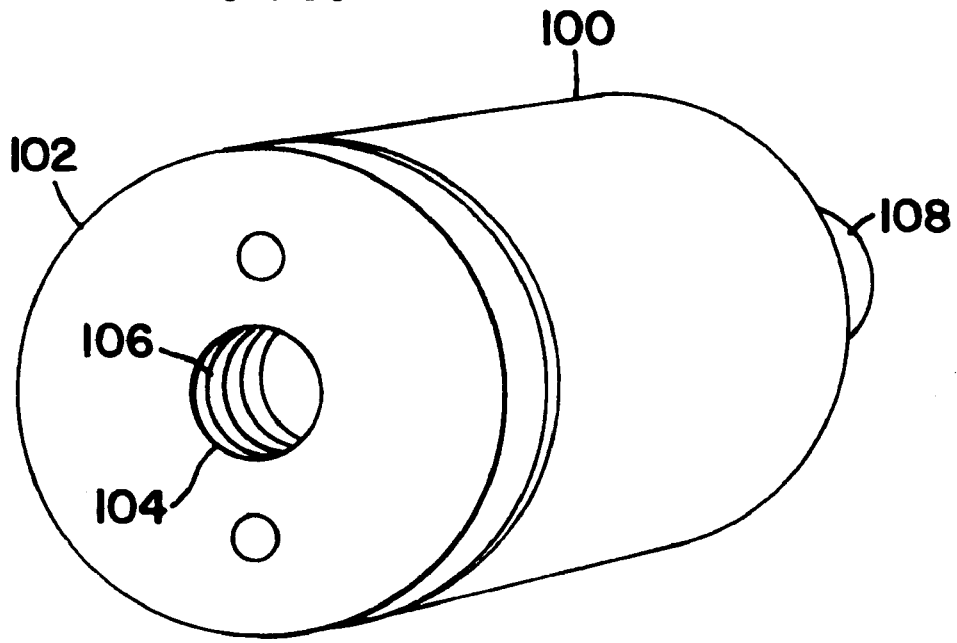
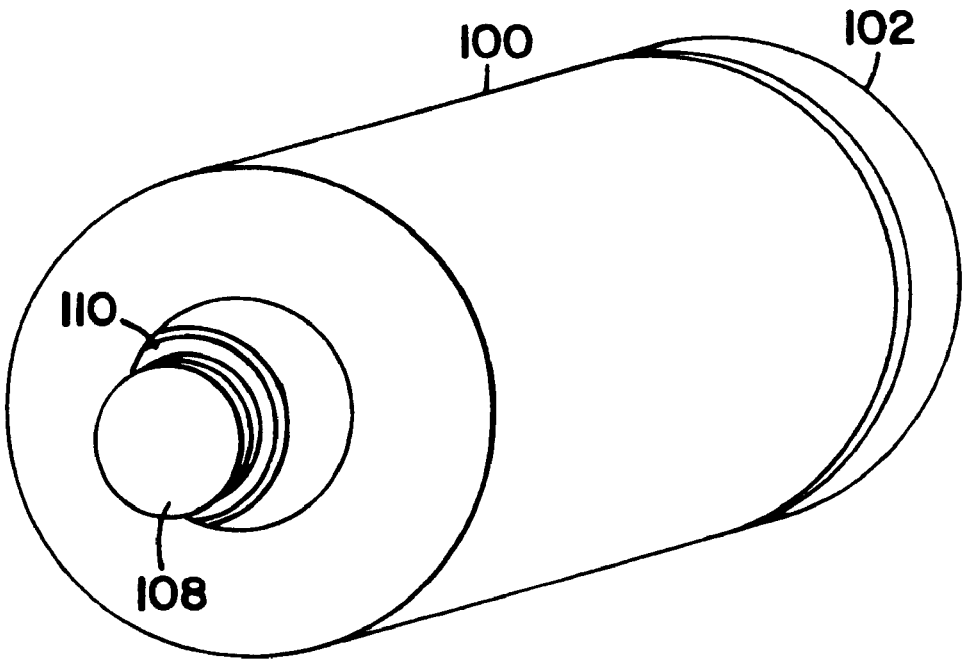
FIG. 18B

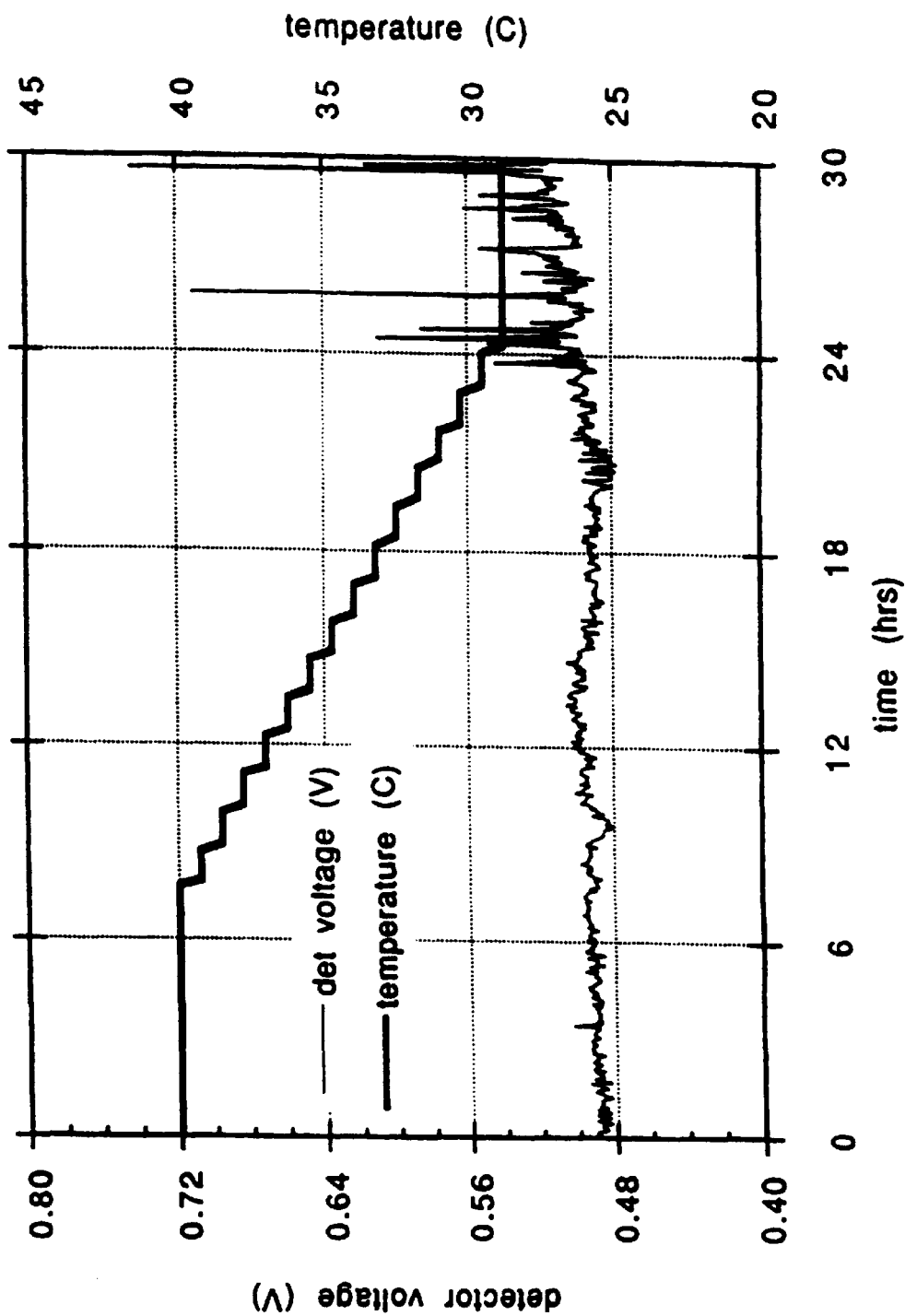

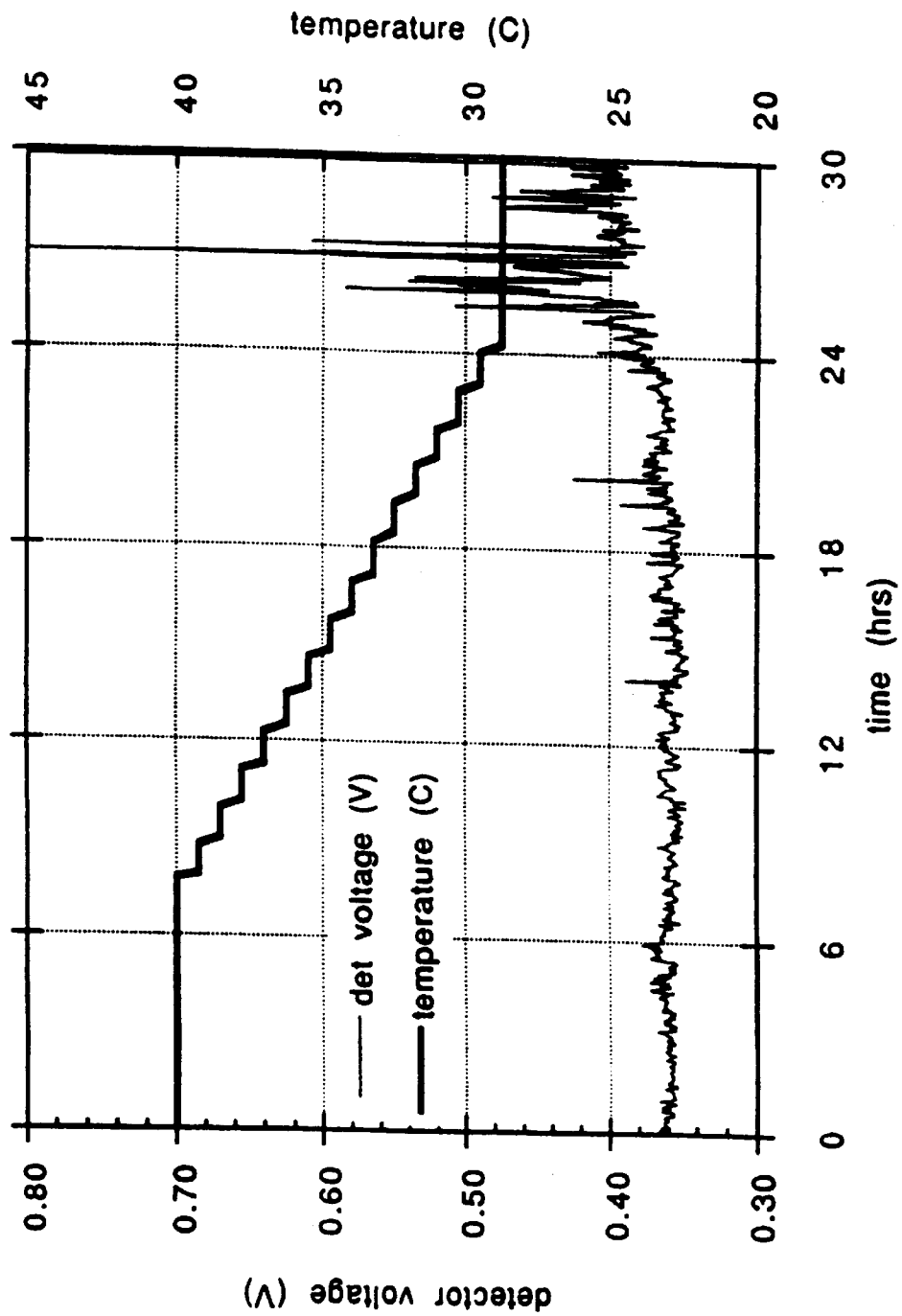

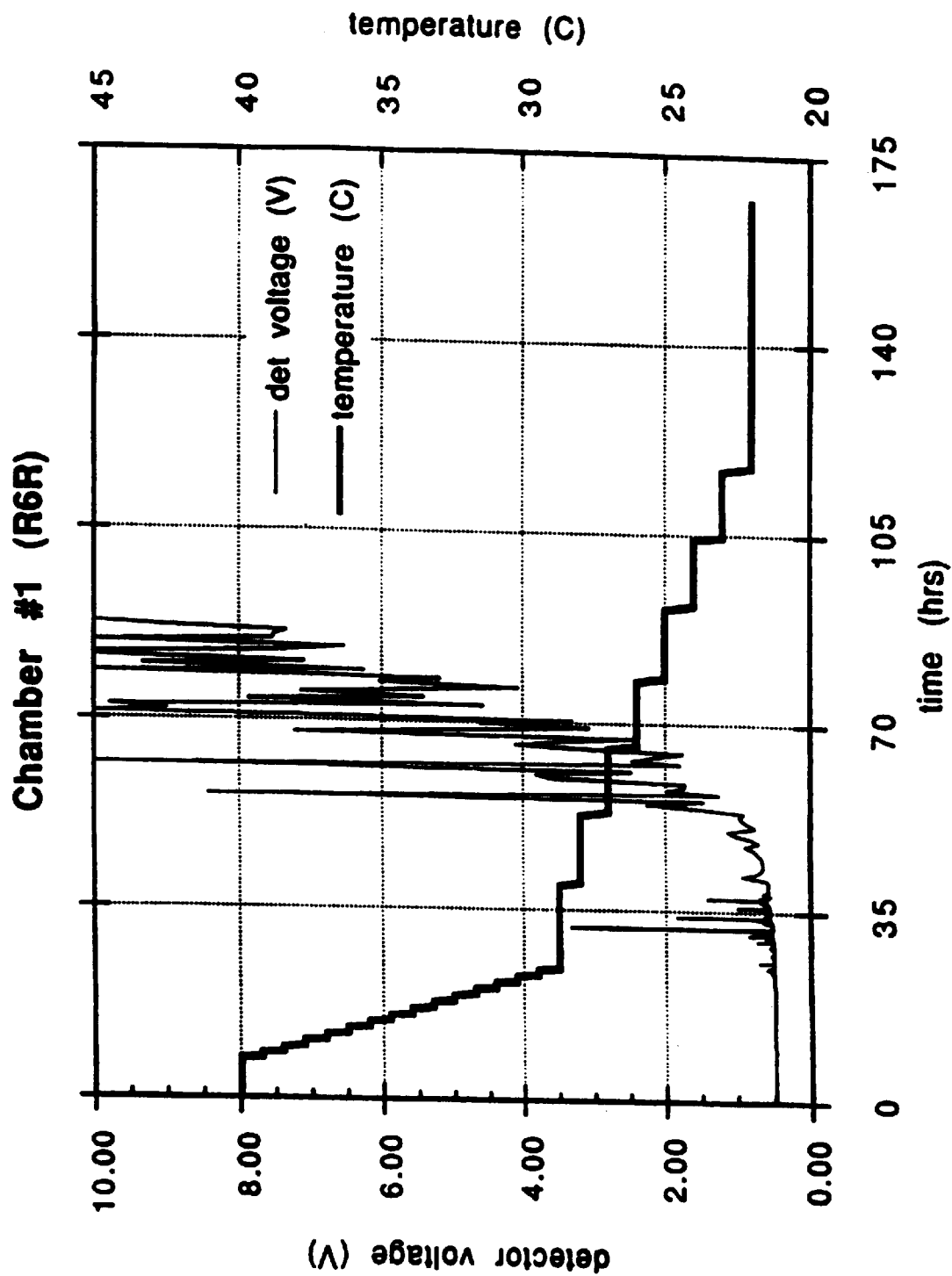

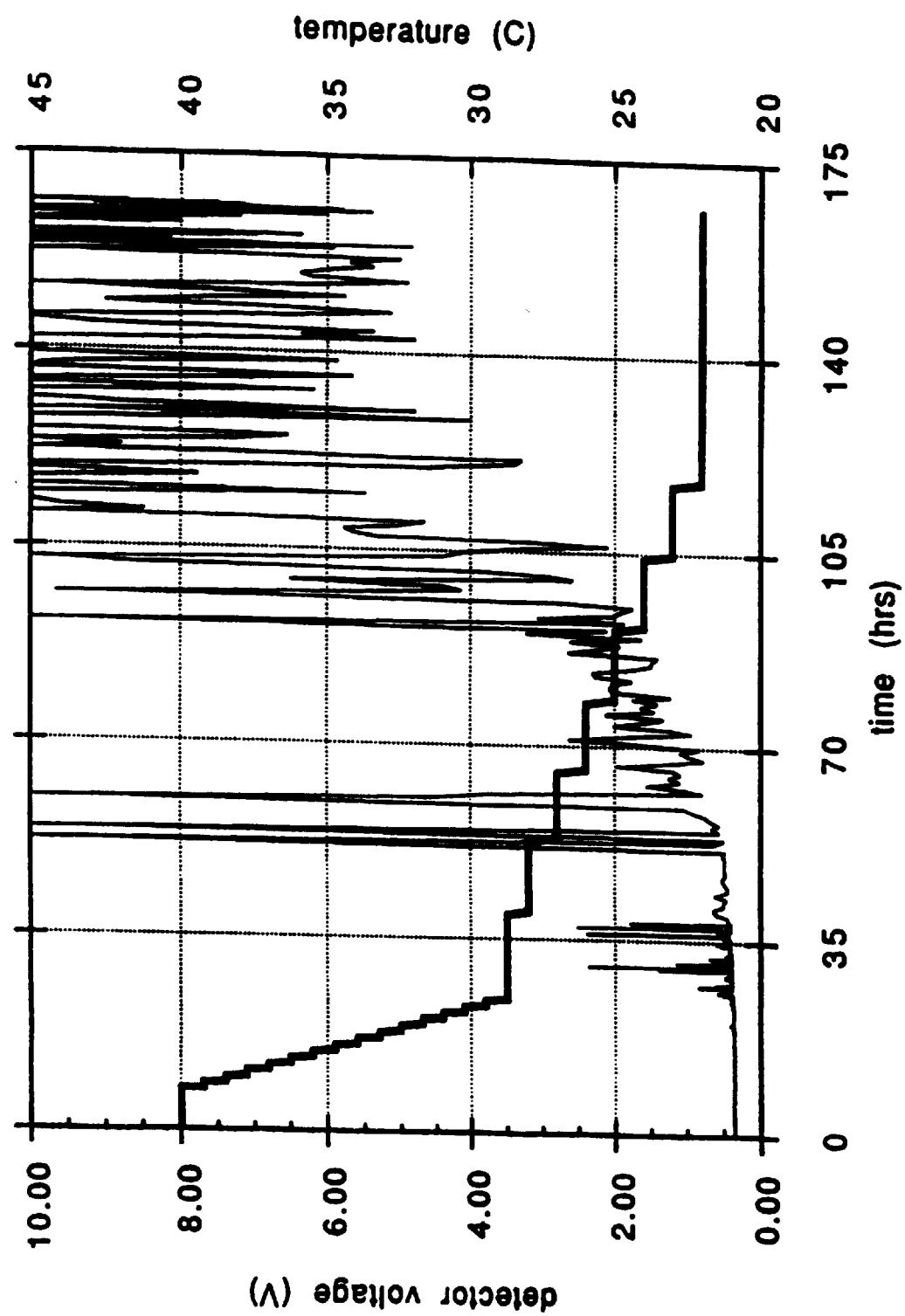

METHOD AND APPARATUS FOR CRYSTALIZING MACROMOLECULES IN MICROGRAVITY

This application is a Continuation-In-Part of application Ser. No. 08/441,256, filed May 19, 1996 now abandoned. Application Ser. No. 08/441,256 is a continuation of application Ser. No. 08/281,865 filed Jul. 28, 1994, now abandoned. Application Ser. No. 08/281,865 is a continuation of application Ser. No. 08/076,948 filed Jun. 16, 1993, now abandoned. Application Ser. No. 08/076,948 is a continuation of application Ser. No. 07/836,658 filed Feb. 18, 1992, now abandoned. Application Ser. No. 07/836,658 is a continuation-in-part of application Ser. No. 07/659,948 filed Feb. 25, 1991, now abandoned.

FIELD OF THE INVENTION

The present invention relates to a method and an apparatus for crystallizing biological macromolecules such as proteins. In particular, it relates to an apparatus for crystallizing biological macromolecules in microgravity.

BACKGROUND OF THE INVENTION

One need for purified protein is derived from the pharmaceutical industry's interest in protein products as therapeutic agents. Protein therapeutic agents can be used in humans against any number of diseases, including cancer, immunodeficiency diseases and various types of infections. However, since many medicinal proteins are prepared from genetically engineered bacteria, procaryotic protein impurities can present costly problems in final purification steps. It is essential to remove these contaminants because they are immunogenic. If the contaminants are allergenic, even minute amounts can cause significant adverse side reactions. Accordingly, protein therapeutic agents must be extremely pure.

Over the past ten years there has been an exponential growth in protein pharmaceuticals. Human insulin, interferons, human growth hormone, TPA (tissue plasminogen activator) and erythropoietin are examples. This is so mainly because of genetic engineering techniques which allow for the large scale microorganism synthesis of proteins that occur in minute amounts in the human body.

It is known to grow protein crystals in microgravity using hanging drops in a vapor diffusion apparatus (VDA). However, the disadvantage of this method is that it produces limited amounts of crystals because the volume of the hanging drop is small, i.e., 0.05 mL. The yield is sufficient to supply research amounts of the protein crystals for x-ray crystallography, but cannot be considered a large scale method that could provide bulk amounts of protein crystals. Another limitation of the hanging drop method, which again is due to the small sample size, is the problem of droplet surface effects. Flow patterns on the surface may adversely affect protein crystal growth.

SUMMARY OF THE INVENTION

One embodiment of the invention is an apparatus for producing crystals of a macromolecule in microgravity. The apparatus includes a container which is open at one end and is made of a material having a low thermal conductivity. A thermally conductive lid is fitted on the open end of the container to close the container and a heat source/sink is provided in thermal contact with the thermally conductive lid to generate a temperature gradient within the container.

In one aspect of the invention, the containers are adapted to be stackable, one on top of the other. For example, the cap may contain a recess which is adapted for receiving an extension of a second container which protrudes from the closed end of the second container directly opposite the cap.

In another aspect of the invention, a light source and detector are aligned around the container. The light source illuminates a solution in the container and the detector measures the amount of light scattered by crystals or crystal nuclei in the container. As macromolecules in the solution crystallize, there is an increase in scattered light which is measured by the detector.

Another embodiment of the invention is a method for the production of crystals of a macromolecule in microgravity. The method includes introducing a container holding a solution of the macromolecule and a precipitating agent into a microgravity environment. The container has sidewalls and a closed end formed from a material having a relatively low thermal conductivity. The container also has an open end and a thermally conductive lid fitted on the open end. The thermally conductive lid is in thermal communication with a heat source/sink. The method also includes generating a temperature gradient in the solution by altering the temperature of the heat source/sink and thereby altering the temperature of the thermally conductive lid. The temperature of the heat source/sink is changed over time to maintain the temperature gradient and induce and control growth of crystals of the macromolecule. In this manner, crystals of the macromolecule are formed by aggregation of the macromolecule in response to the temperature gradient. The crystals have one or more enhanced characteristics when compared to crystals of the macromolecule produced in a normal earth gravity.

BRIEF DESCRIPTION OF THE DRAWINGS

The following figures are provided to illustrate a preferred embodiment of the present invention.

FIGS. 18a and 18b are perspective views of the top and bottom, respectively, of the stackable PCF bottle of FIG. 17;

FIG. 21 is a graphical representation of the temperature ramp and output voltage of the light scattering measurement device of FIG. 19 for an insulin sample;

FIG. 22 is a graphical representation of the temperature ramp and output voltage of the light scattering measurement device of FIG. 19 for another insulin sample;

FIG. 23 is an expanded graphical representation of the temperature ramp and output voltage of FIG. 21 over a longer period of time;

FIG. 24 is an expanded graphical representation of the temperature ramp and output voltage of FIG. 22 over a longer period of time;

DETAILED DESCRIPTION OF THE ILLUSTRATED EMBODIMENTS

Figure 1:
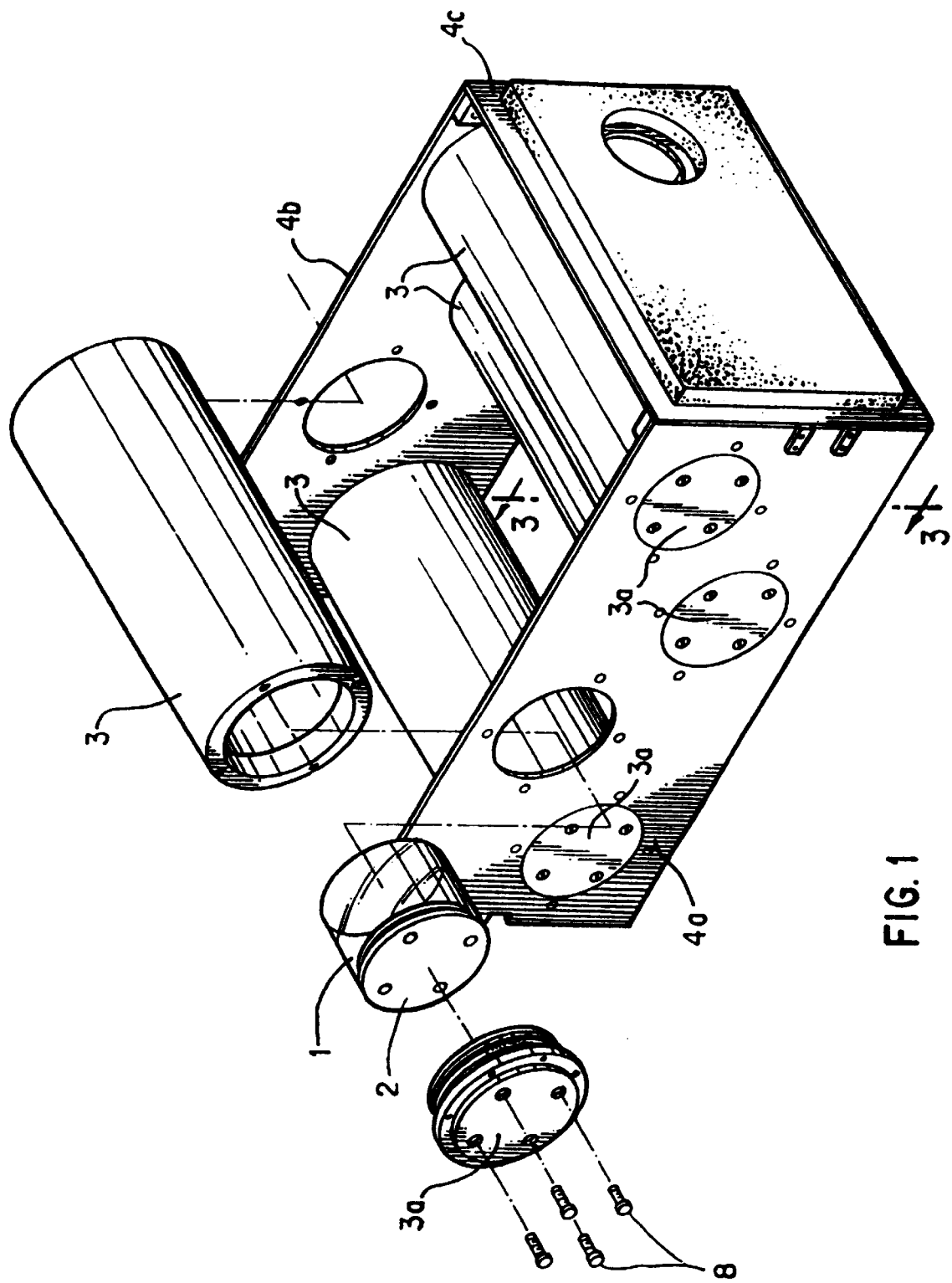
FIG. 1 is a partially-exploded perspective view of a Protein Crystallization Facility (PCF) according to one embodiment of the invention.
Figure 1B:
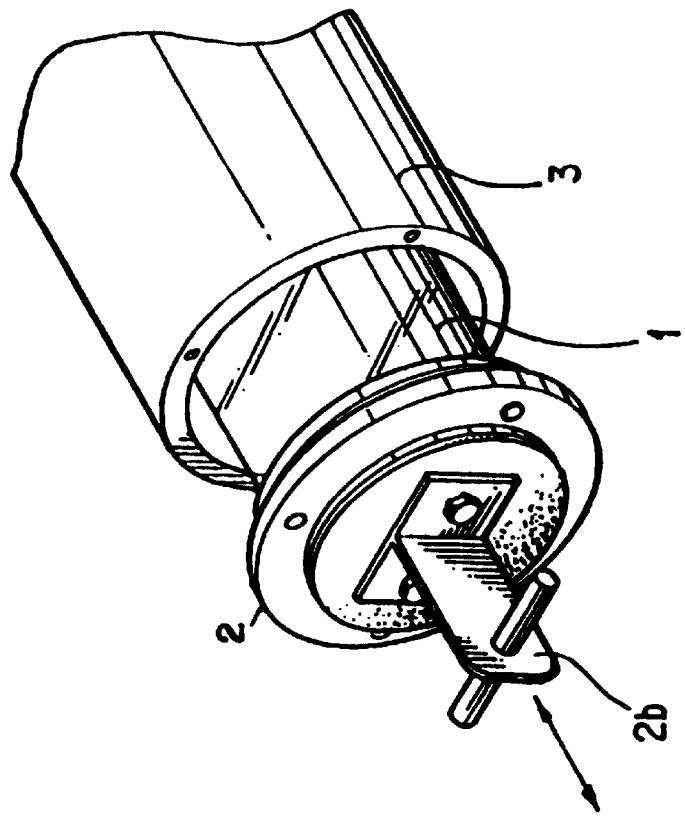
FIG. 1B is a perspective view of showing a t-handle attached to a lid of a bottle in the PCF of FIG. 1.
Figure 1A:
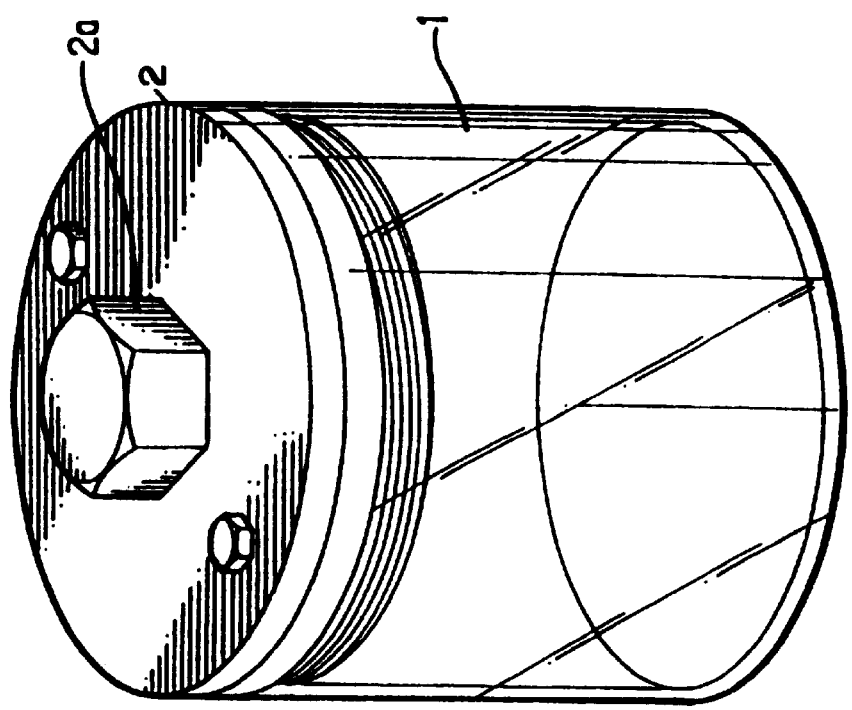
FIG. 1A is a perspective view showing a torquing tool attached to a lid of a bottle in the PCF of FIG. 1.

The apparatus for producing crystals of a macromolecule includes one or more containers for holding a macromolecule-containing solution. These containers are typically formed of a material which has low heat conductivity. The containers also have an open end which, after the container is filled, is covered by a thermally conductive cap. During operation of the apparatus the thermally conductive cap is placed in contact with a heat source/sink which is capable of driving a temperature change in the containers, either by heating or cooling. This generates a temperature gradient in the containers which results in the production of crystals of the macromolecule.

One embodiment of a crystallization apparatus, according to the invention, is illustrated in FIGS. 1–10 and is made up of four Polymer Crystallization Facilities (PCFs) which, in this embodiment, are polysulfone PCF bottles 1 with aluminum PCF caps 2 capable of containing a protein solution to be crystallized. The crystallization device also includes four aluminum cylinders 3 having aluminum cylinder tops 3a at one end and stem and purge valves at the other end (see FIG. 6), two side plates 4a–b, one front panel 4c, attachment hardware including rails 6 (see FIG. 2) and springs, and four stem-and-purge caps 7 (see FIG. 6).

The apparatus comprises four PCF bottles 1 which are heated or cooled at one end to initiate protein crystal growth. The PCF bottles are made of polysulfone, which has the advantages of being qualified for space flight, relatively inert to protein adhesion, transparent and pliant enough to withstand temperature fluctuations in the 4° C. to 60° C. range. Although PS-1700 polysulfone is preferably used, any material which is nonadherent to proteins could be used for the PCF bottles. The four PCF bottles 1 may be of the same diameter but of different heights and, accordingly, different volumes. The different heights allow a different temperature gradient to be obtained in each bottle. Once the appropriate temperature gradient has been determined for a particular protein, bottles of same height and different diameters can be used. In other embodiments of the invention, the PCF bottles may have the same height with varying diameter to provide bottles with different volumes. Alternatively, the PCF bottles may all be of the same size.

An optional coating may be applied to the interior of the PCF bottles to reduce the adhesion of macromolecule crystals. Such a coating is typically applied prior to introduction of a sample into the PCF bottle and may need to be reapplied with each use of the PCF bottle. The particular choice of coating may be macromolecule-dependent.

The volumes of the PCF bottles in the embodiment illustrated in FIGS. 1–10 are 500, 200, 100 and 50 mL, but the bottles can be of any volume as long as they fit inside of a refrigerator-incubator module (RIM) 5 (see FIG. 4) or other thermally controllable unit. Each PCF bottle or container is closed with a threaded metal V-shaped cap 2 using a single O-ring so that the cap 2 serves as the pathway for heating or cooling. The "V-shape" of the bottom portion of the cap 2 functions to push bubbles out of the bottle when the cap is being placed thereon. The cap 2 may be coated with a barrier material to separate the metal of the cap 2 from the macromolecule-containing solution. One example of a suitable barrier material is Teflon. The foregoing embodiment of the present invention using bottles of different size allows evaluation of crystal size and quality as a function of the different temperature gradients obtained because different proteins require different gradients for optimal crystal growth.

The RIM itself is a known device. It is a solid-state (semiconductor) heating and cooling device designed to regulate an internal cavity temperature adjustable to within 0.1° C. with an external knob adjustment. Specifically, the RIM is a six-sided box, one side of which is a door. The six sides comprise a double-walled structure, the external walls of which are reinforced fiberglass and the interior walls of which are heat-conducting metal. Five of the six double walls contain insulation therein. The sixth double wall, the interior wall of which is termed the cold plate, houses a thermal control unit (TCU). The TCU is a well known device made up of a thermal electric unit (TEU), a heat exchanger, a temperature-feed-back sensor, and a fan. The TEU is a well known plate-like unit sandwiched between the cold plate and the heat exchanger which is also plate-like. Depending upon the direction in which electric current passes through the TCU, heat is either applied to or withdrawn from the cold plate, thereby regulating the temperature in the internal chamber of the RIM. In this manner, the TCU acts as a heat source/sink. The TCU operates to maintain the temperature inside the chamber within 0.5° C. of the set temperature, which is set between 0–40° C. by a knob on the outside of the RIM which may be equipped with a digital temperature readout. In a normal horizontal position, the RIM door, the interior wall of which carries a rubber gasket, is hinged on the bottom, and the cold plate is the left vertical wall of the internal chamber.

For structural support, the RIM is housed inside a metal frame covering the edges of the RIM box and joined at the corners.

Optionally, the PCF bottles may include one or more temperature measurement devices placed along the bottles to determine the temperature gradient. One example of a suitable temperature measurement device is a thermistor which varies in resistance with temperature. These measurements of temperature may be provided on a display and/or to a computer for storage.

The RIM may be operated manually requiring that an operator adjust the temperature. Alternatively, the RIM may be computer controlled (CRIM) with the computer ramping the temperature according to programming.

The readings from the temperature measurement devices may also be used to adjust and control the temperature gradient. For example, if the temperature of the RIM is manually adjustable, an operator can observe the readings from the temperature measurement devices and adjust the temperature gradient accordingly. If the RIM is computer controlled, the computer may use the readings from the temperature measurement devices to update the temperature of the heat source/sink so that the proper gradient is provided.

Aluminum cylinders 3 are used to hold the PCF bottles in place and apposed to a thermal control device of the RIM 5. The cylinders 3 are provided with aluminum cylinder tops 3a to which the PCF caps are attached using four screws. In this way, the bottles are cantilevered within the cylinders, thus allowing ample air insulation around the bottle within each cylinder. The stem and purge valves (see FIG. 6) are used for ground-based leak testing only and are securely covered by stem-and-purge caps 7 when the apparatus is in use.

Figure 2:
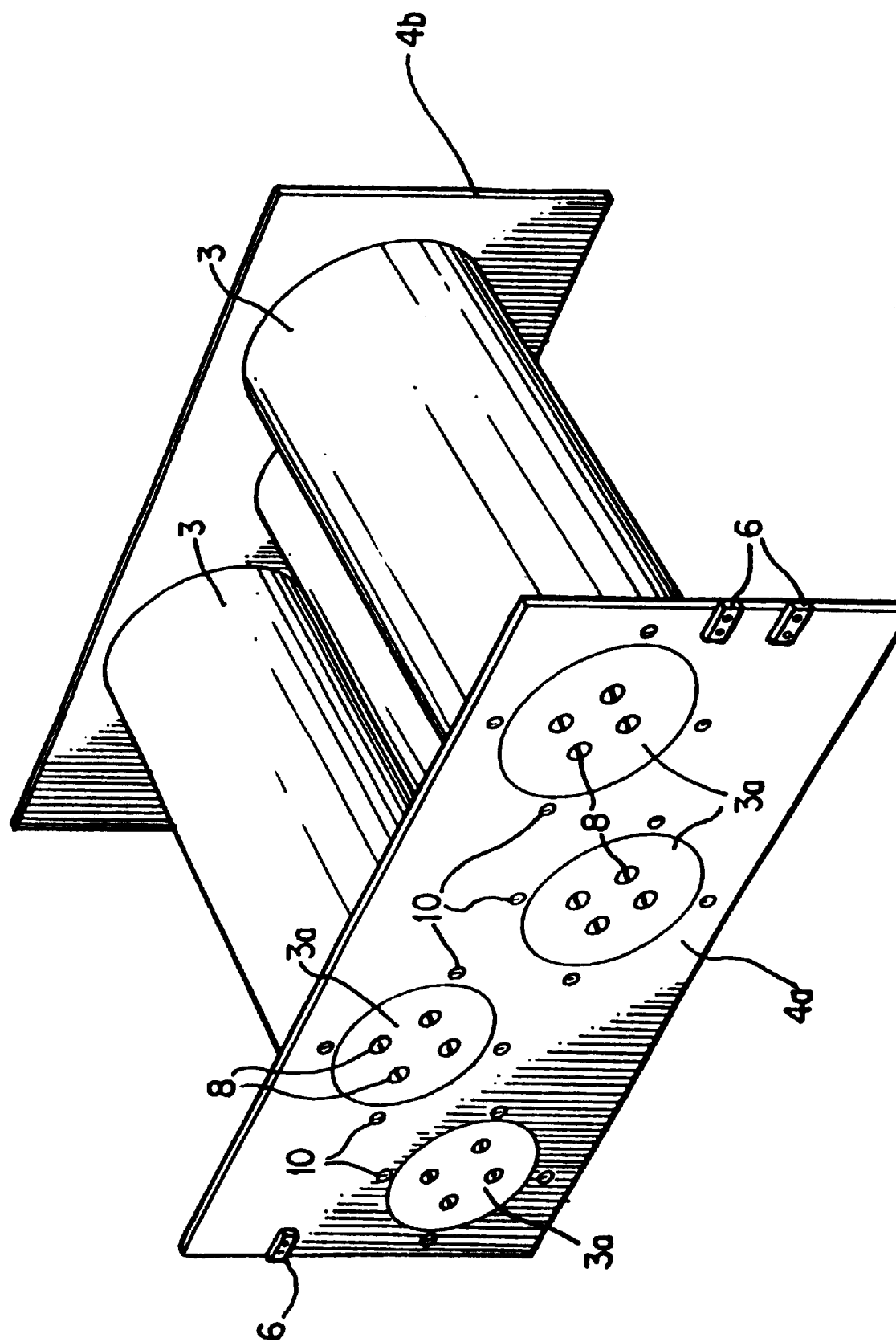
FIG. 2 is a perspective view of the aluminum assembly for the PCF of FIG. 1 with all of the cylinders in place according to the invention.
Figure 3:
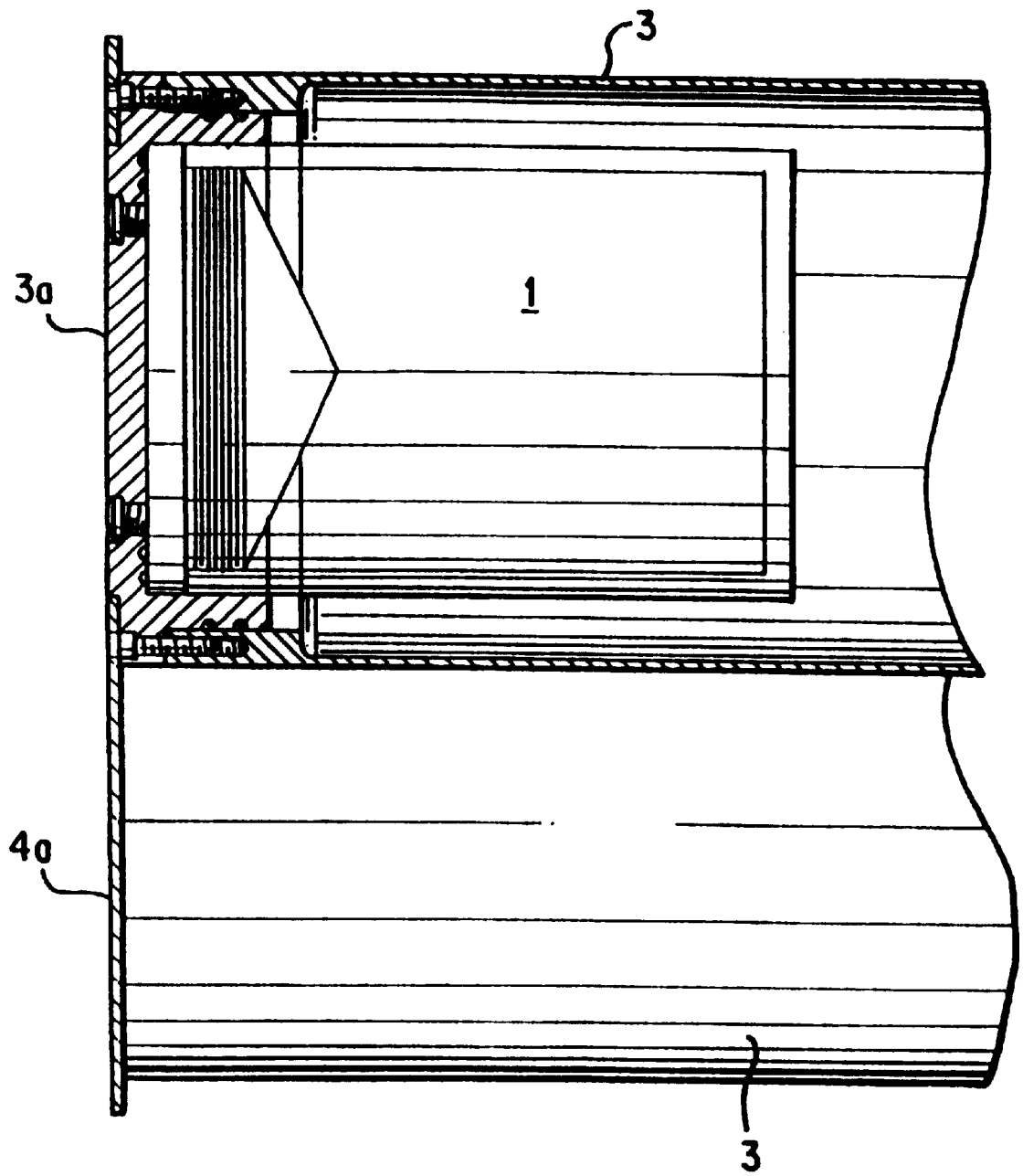
FIG. 3 is a cross-sectional taken along line 3—3 in FIG. 1.

Each aluminum cylinder 3 is a cylindrical, hermetically sealed vessel sandwiched between aluminum side plates 4a–b and fastened to them with screws 10 (see FIG. 2). An aluminum front 4c is attached at one end of the side plates 4a–b. Each cylinder is identical in size. The primary functions of the cylinders are to thermally isolate the PCF bottles from each other, to retain the bottle contents and the bottle in the event that the bottle leaks or fails structurally, and to hold the PCF bottles in the RIM 5 for thermal control. For the latter function, the aluminum cylinders 3 pass through the left side plate 4a so that the aluminum cylinder top 3a, and thus the aluminum PCF cap 2, are in direct thermal contact with the RIM 5 thermal plate.

Figure 4:
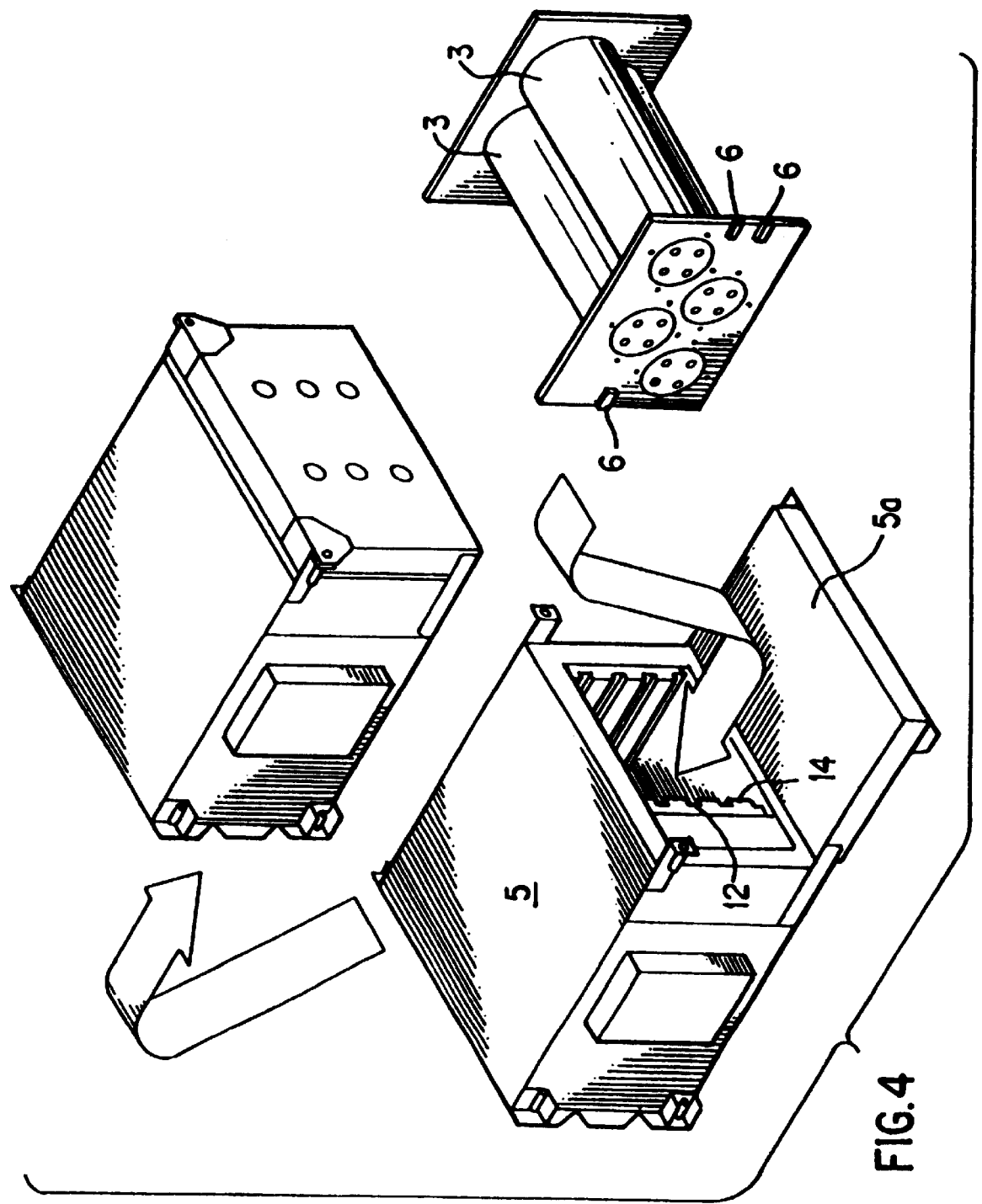
FIG. 4 is perspective view showing insertion of the aluminum assembly of FIG. in the refrigerator-incubator module (RIM)

Rails 6 (see FIG. 2) are bolted to the side plates 4a–b, and these rails are fitted in machined slots 12 in the RIM 5 sidewalls (see FIG. 4). The positions of the rails on the side plates can be changed to accommodate different RIMs. The whole unit is prevented from sliding out of the RIM 5 by the RIM door 5a which is bolted to the front of RIM 5.

Preferably, the aluminum front plate 4c is provided with a foam layer, as shown in FIG. 1, to ensure a snug fit within the RIM once the door 5a has been closed. Any foam material could be used for this layer, but Pyrel from Scott Foam is preferable as it is flame-retardant and has been approved for space flight by NASA.

The aluminum front plate 4c is provided with a circular aperture as shown in FIG. 1. This aperture is provided to cooperate with a pressure release valve of the RIM. The pressure release valve, which is shown from the exterior of the RIM in FIG. 10, prevents implosion or explosion of the RIM when sudden changes in pressure occur.

Figure 8:
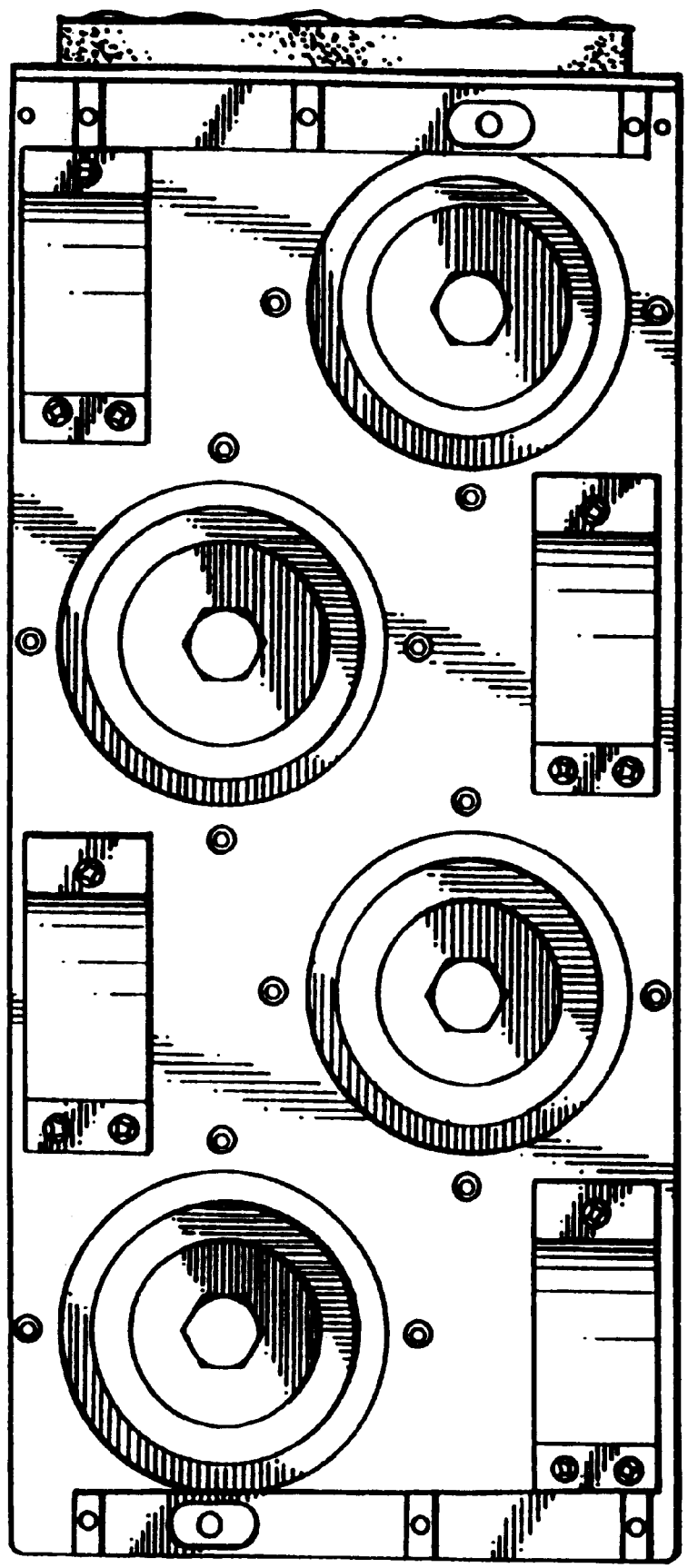
FIG. 8 is a side elevational view showing the assembly of FIG. 2 with the front panel in place from the right side.
Figure 9:
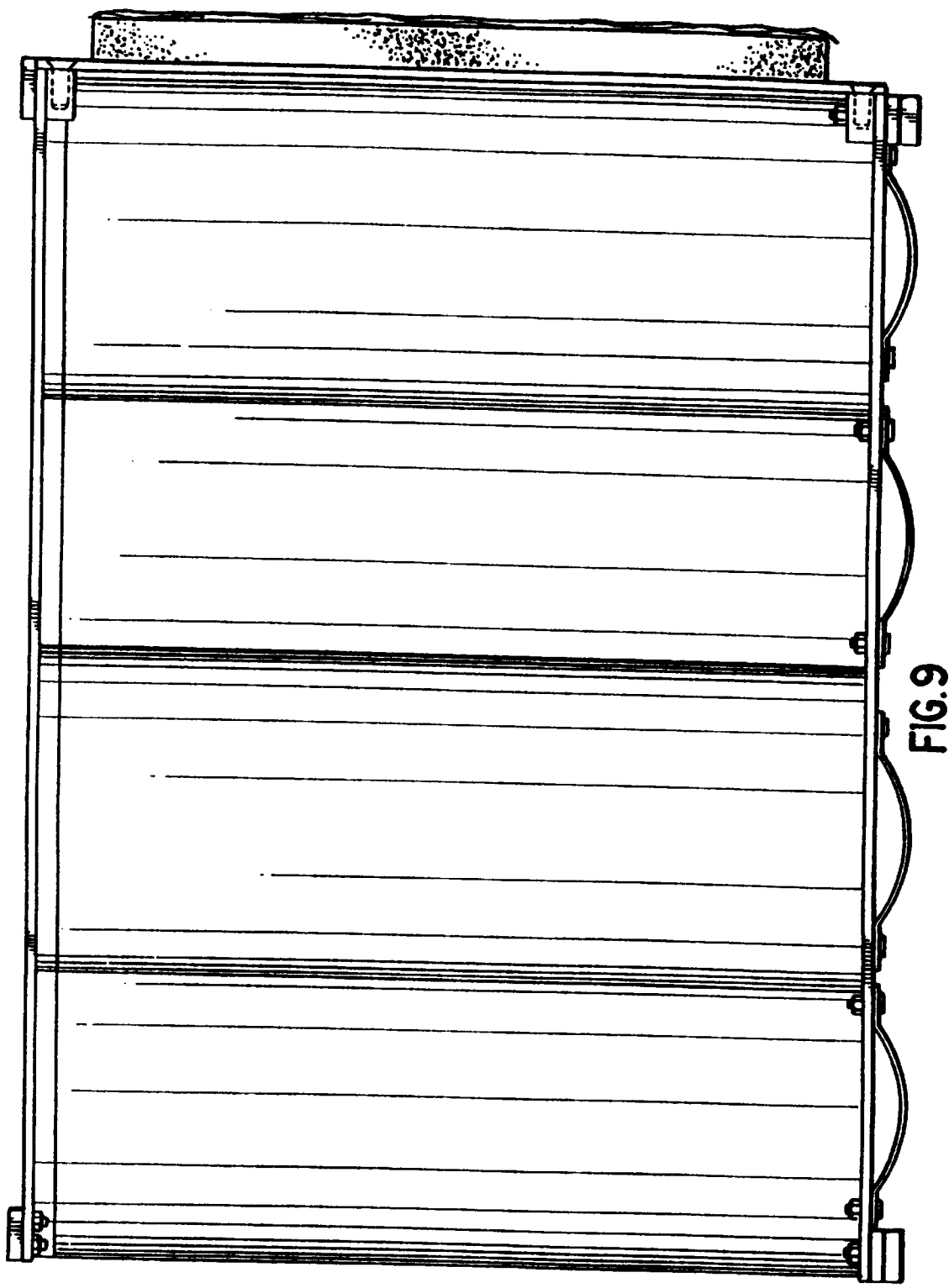
FIG. 9 is a bottom plan view of the assembly of FIG. 2.
Figure 10:
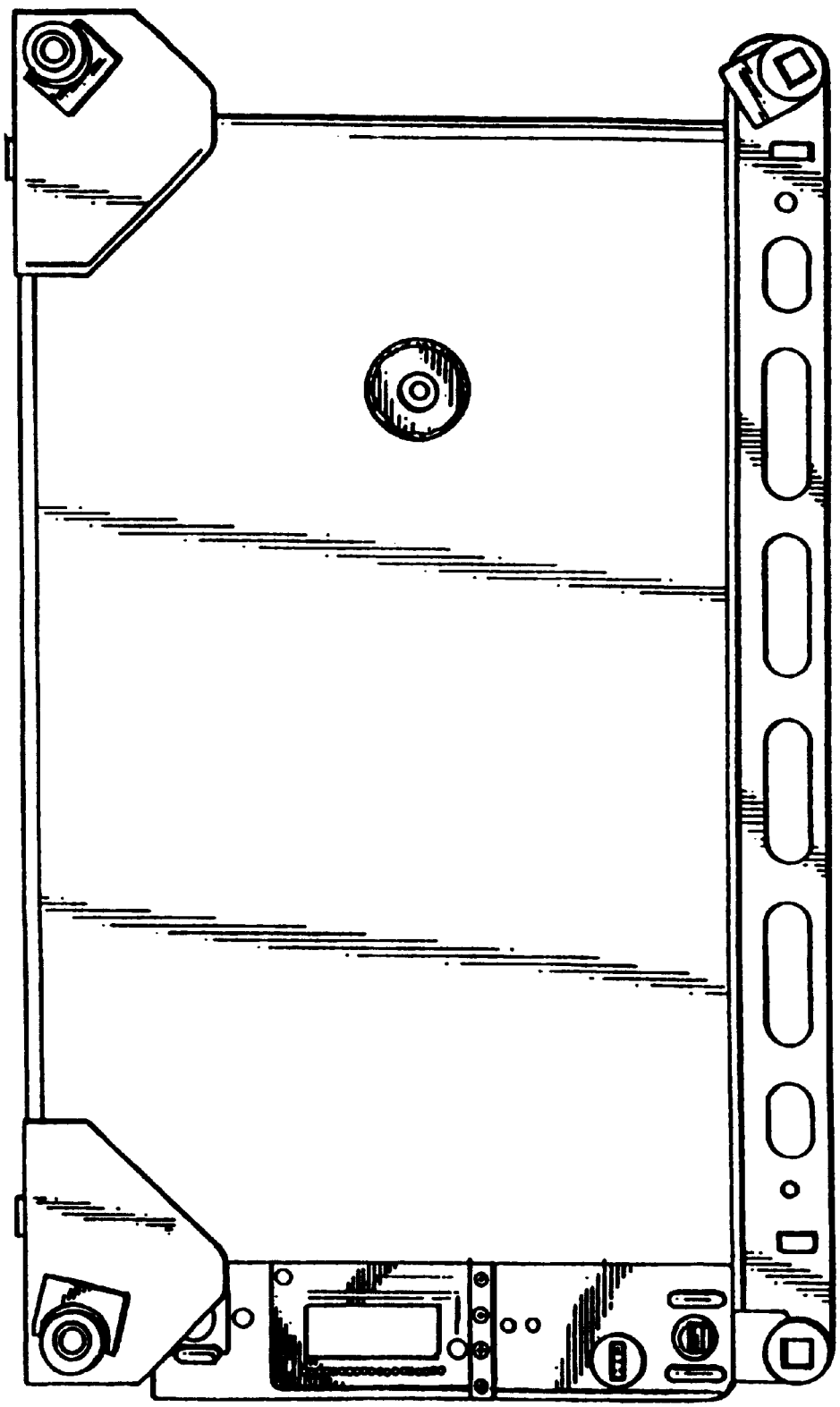
FIG. 10 is a top plan view of the RIM of FIG. 4 showing the pressure release valve.

The left side plate 4a is used as the thermal plate. Since one of the primary objectives of the RIM 5 during the PCF operation is to provide identical thermal environments to the bottles, it is very important that the interface between the thermal plate and the top of the sample container be highly conductive. For this reason, the PCF is designed so each aluminum PCF cap 2 is screwed to the aluminum cylinder top 3a of the corresponding cylinder 3 and the aluminum cylinder top 3a feeds through the left side plate 4a to the thermal plate of the RIM 5, thus giving a good conductive path to the protein solution. As shown in FIG. 8, the right end plate also uses a series of leaf springs to help keep the PCF pushed up against the thermal plate of the RIM 5.

The RIM door 5a remains closed at all times when the apparatus is flown. The only required crew operation is the adjustment of a temperature control knob located on a control panel of the RIM 5.

As an example of operation of the RIM and PCF, the temperature is set at 40° C. while the RIM is being placed in the Orbiter and remains at that temperature during the initial phase of the flight. Then, during the first 24–48 hours of the flight, the temperature is lowered from 40° C. to 22° C. After the temperature adjustment of the RIM 5 is complete, the PCF environment requires no more crew activity with the exception of occasional monitoring to ensure that the RIM 5 is holding the correct temperature.

As an example of sample preparation, for bovine insulin samples, the following materials can be used: bovine insulin 24 I.U. per mg., crystalline, 0.5% zinc content (available from Sigma Chemical Co., St. Louis, Mo. under cat. no. 15500), protamine (salmine sulfate) from salmon, grade II (available form Sigma under cat. no. P4380) and m-cresol (3-methylphenol), approximately 99% (available from Sigma under cat. no. C5015); and sodium phosphate (dibasic heptahydrate) and sodium chloride (certified A.C.S. grade available from Fisher Scientific, Fair Lawn, N.J.).

Bovine insulin samples at 1.6 mg/mL to 0.2 mg/mL are prepared in 0.01M $Na_2HPO_4$, 0.5 M NaCl and 0.3% m-cresol, pH 6.5. The samples are incubated at 60° C. for 10 minutes to facilitate the insulin dissolution and cooled at room temperature for 5 minutes afterwards. Then, a 1.0% solution of salmine sulfate is added such that the ratio of milligrams salmine sulfate to milligrams insulin is 0.125. The resulting suspension is warmed to 60° C. and incubated at 60° C. for 60 minutes to dissolve as much of the amorphous precipitate as possible. The sample is filtered through a 0.22 micron nylon filter (Rainin, Woburn, Mass.) at 60° C. and the resulting filtrate is allowed to cool slowly by placement in a programmable water bath and lowering the temperature of the bath from 60° C. to 40° C. in a linear fashion over 24 hours. The filtrate is then poured into four prewarmed PCF bottles 1 and the visible bubbles clinging to the inside wall are removed with a tetrafluoroethylene-coated spatula at 40° C. The insulin solution fills the bottle to such an extent that when the aluminum PCF cap 2 is screwed on there are no visible air bubbles. The conical shape of the PCF cap 2 is designed to displace any remaining air bubbles that would otherwise become trapped in the bottle. After the bottle is filled, the cap is screwed down to a specified torque. To facilitate this operation, a torquing tool 2a may be used. Each of the four PCF bottles 1 are filled in this manner at 0–45° C. and then each is placed in the corresponding aluminum cylinder 3. Placement and removal of the PCFs may be facilitated by using a T-handle 2b temporarily attached to the aluminum cylinder top 3a. The cylinder 3 is in turn placed in an assembly comprising the two side plates 4a–b and the front panel 4c which interfaces with the RIM 5. Again, all of these operations are done at 40–45° C.

The PCF loading procedure according to a preferred embodiment of the present invention is described in detail below:

1. The PCF bottle is filled with the insulin solution.

Figure 5:
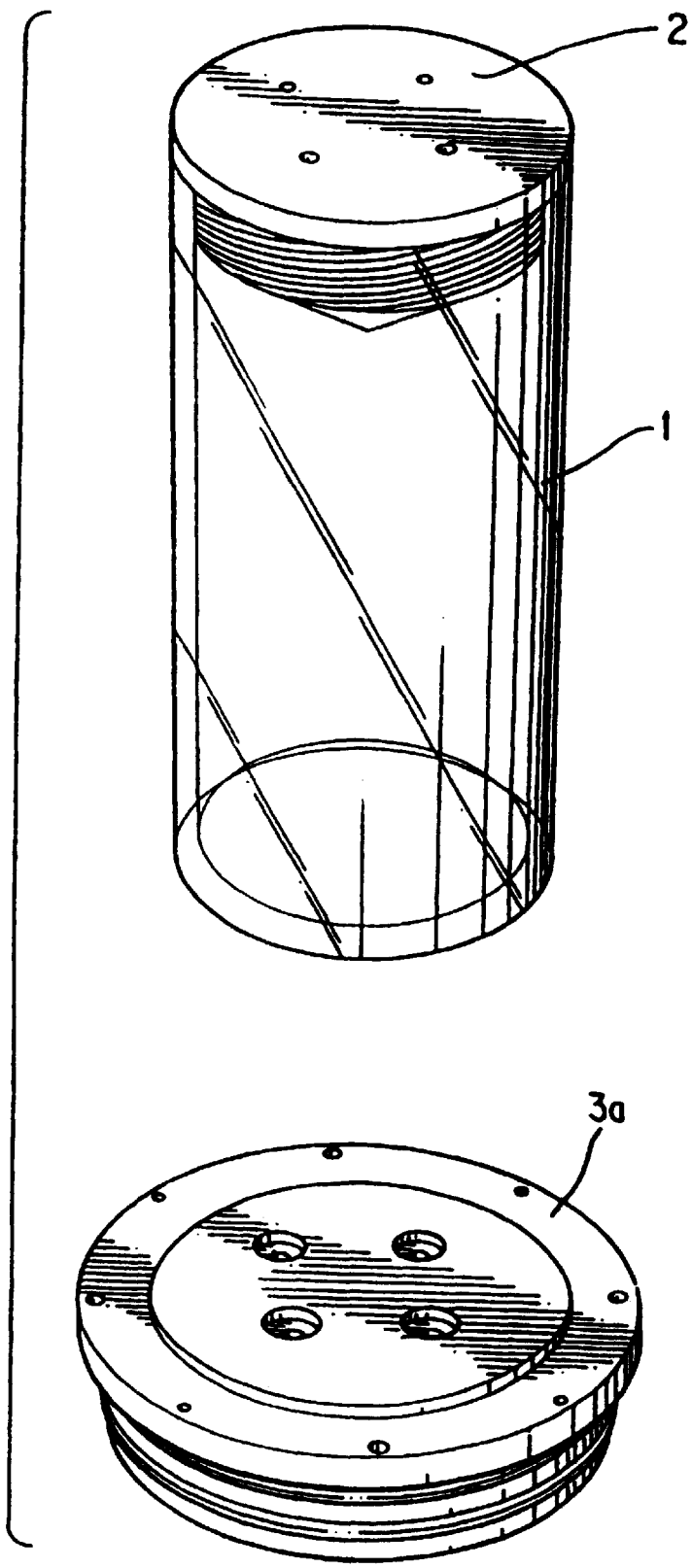
FIG. 5 is a perspective view showing an exemplary PCF bottle with cap torqued to 130 lbs/in and an aluminum cylinder top.
Figure 6:
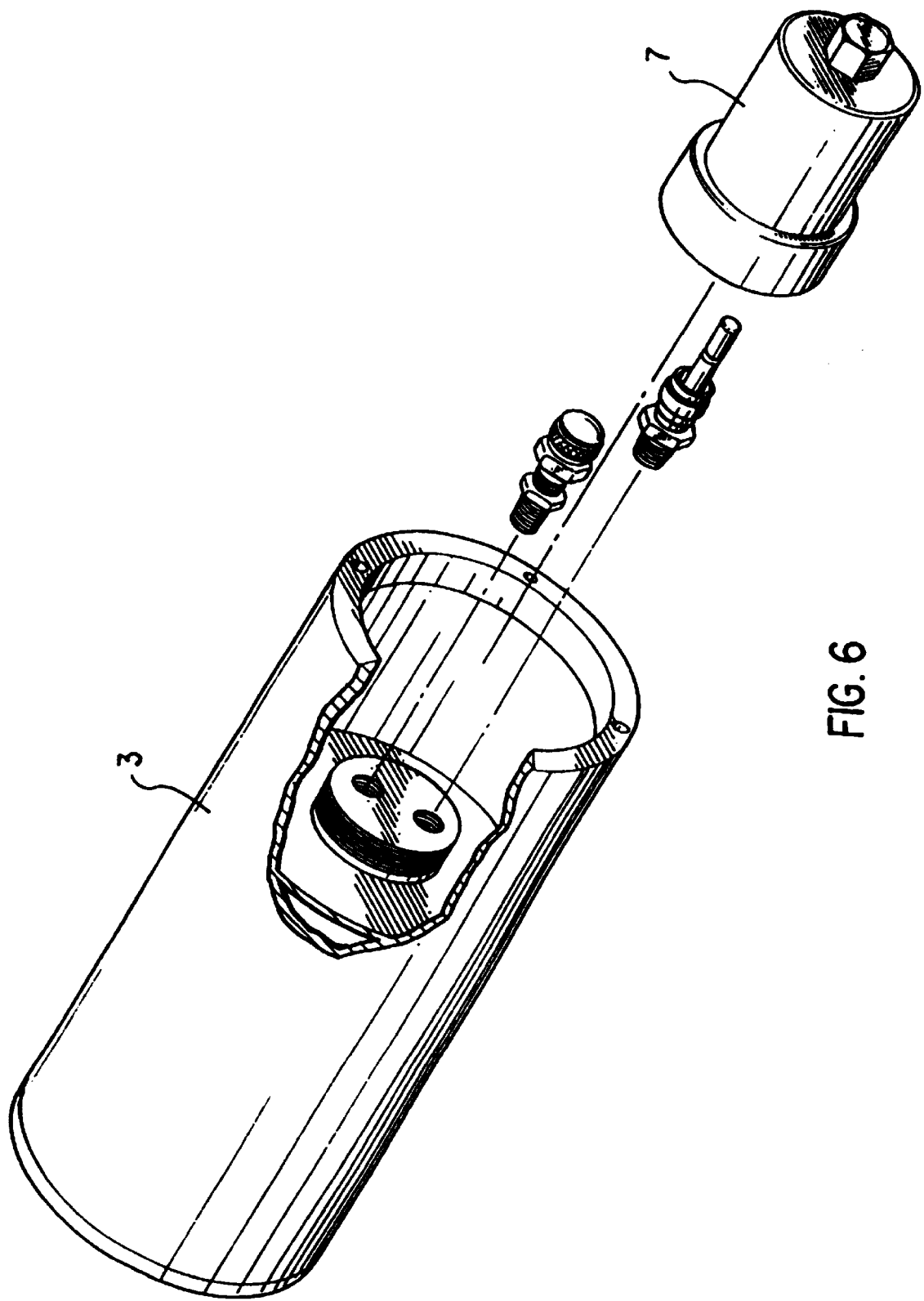
FIG. 6 is an exploded perspective view showing an aluminum cylinder having stem and purge valves and a stem-and-purge cap.
Figure 7:
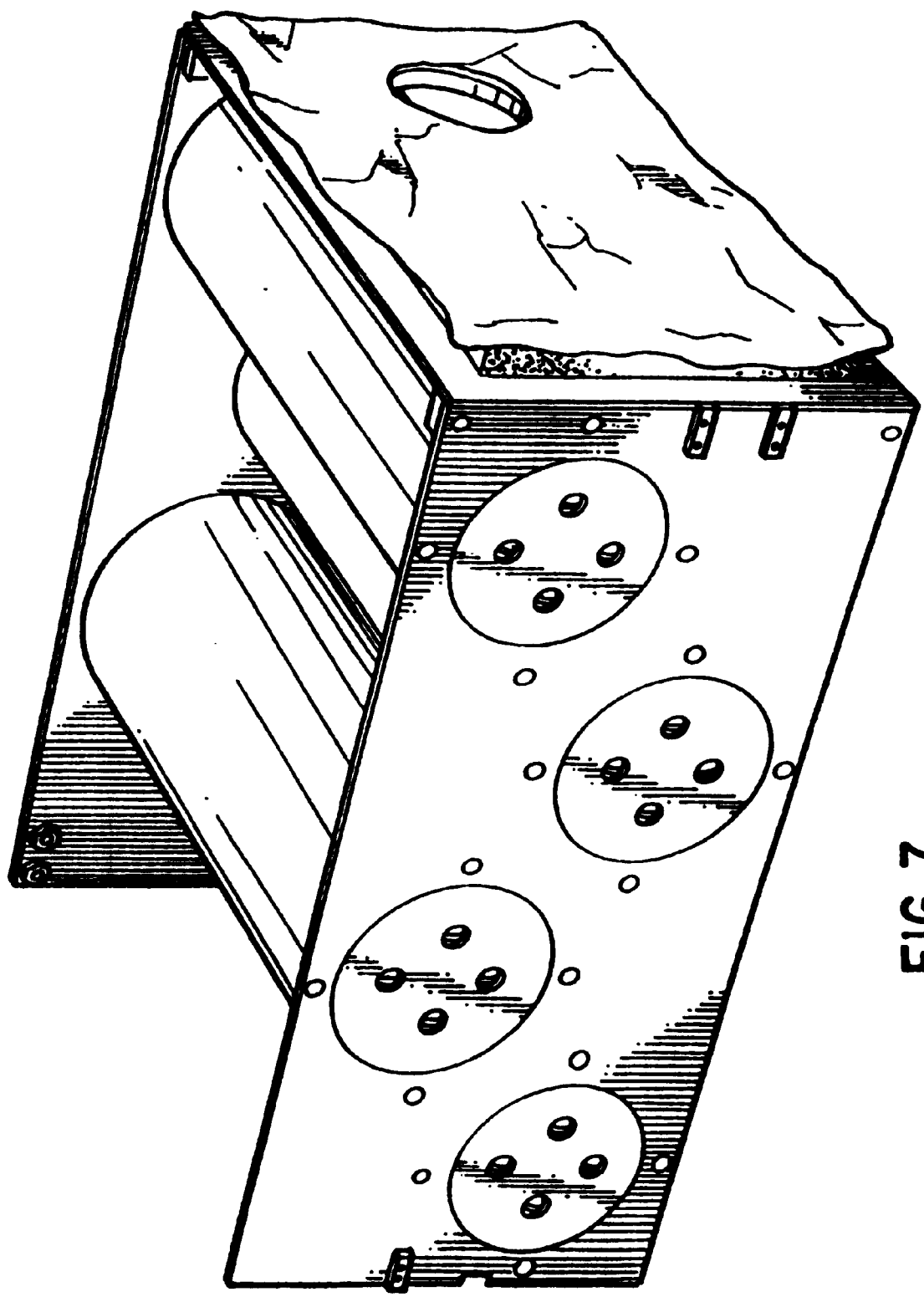
FIG. 7 is a perspective view showing the assembly of FIG. 2 with the front panel in place from the left side.

2. The aluminum cap is screwed onto the bottle. As shown in FIGS. 3a and 5, the shape of the cap pushes any air bubbles out of the bottle.

3. The torquing tool is attached to the top of the cap with four screws.

4. The cap is tightened to about 15 N m (130 in-lbs) with a torque wrench.

5. The torquing tool is detached.

6. The aluminum cylinder top is attached to the PCF aluminum cap with four screws torqued to 0.28 N m (40 oz-in).

7. The assembly is placed in the aluminum cylinder.

8. The assembly is attached to the aluminum cylinder with four screws torqued to 40 oz/in.

9. At the end of the aluminum cylinder opposite to the PCF cap a stem-and-purge cap is attached and torqued to 0.28 N m (40 oz-in).

10. Steps 1–9 are performed for the other PCFs.

11. Each aluminum cylinder is immersed in water to check for air leakage from the cylinder by watching for bubbles.

12. Once the leak test has been passed, the four aluminum cylinders are attached to the right side plate using four screws torqued to 0.28 N m (40 oz-in) for each cylinder.

13. The left side plate is attached to the other end of the cylinders in the same way.

14. The left and right side plates are attached to the front panel with 6 screws torqued to 0.28 N m (40 oz-in).

15. The completed assembly is placed in the RIM, which has been prewarmed to an internal temperature of 40° C.

These operations are done at 40–45° C. so as to keep the bovine insulin solution from going lower than 40° C. prior to loading into the RIM, which is set at 40° C. The RIM 5 remains powered and set at 40° C. until activation in microgravity. Once in orbit, the RIM 5 is cooled from 40° C. to 22° C. over a period of about 26 hours. Four temperature changes are made: 40–36° C. at about 3 hours; 36–32° C. at about 9 hours; 32–28° C. at about 19 hours; and 28–22° C. at about 26 hours.

In another embodiment of the invention, the cantilevered mounting of the PCF bottles within the cylinders may be replaced with stiff insulation to hold the bottle in place within the cylinder. This stiff insulation can be molded or can be introduced into the cylinder as a foam which hardens around the bottle. Pyrel from Scott foam is preferable for the stiff insulation, however any material can be used which has a thermal conductivity value that is less than the thermal conductivity of the solution in the bottle. This is necessary to ensure that heat is not drawn away from the bottle. In addition, the cylinders may be partially and/or fully evacuated of air in order to maximize the insulation properties around the PCF bottle.

In addition, the PCF bottles may be held in place using an internal brace such as a "donut" brace or a ribbed or spoked brace. Furthermore, the PCF bottles may be provided with lengthwise or circumferential extensions corresponding to the inner surfaces of the cylinders.

Figure 17:
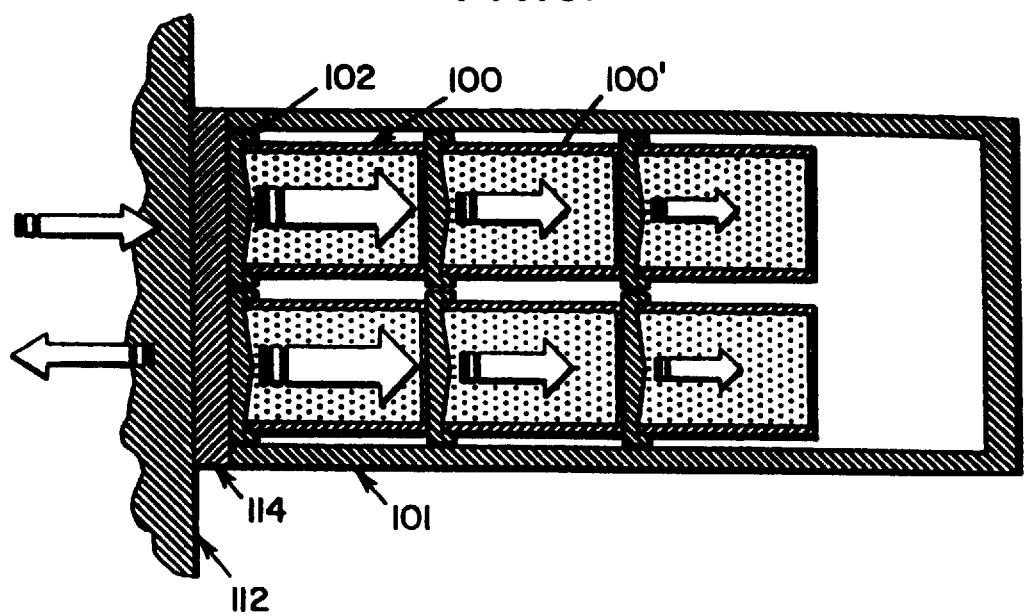
FIG. 17 is a cross-sectional view of a PCF, according to the invention, with stackable PCF bottles.

In a further embodiment of the invention, the PCF bottles 100 are stackable within the cylinder 101, as shown in FIG. 17. The PCF bottle 100 is open at one end and has a thermally conductive PCF cap 102 which covers the open end. The PCF cap 102 has a central recess 104 and threading 106 along the sidewall of the recess, as illustrated in FIG. 18A. The PCF cap is typically made with a metal material, for example, aluminum.

The PCF bottle 100 has an extension 108 protruding from the end opposite the cap 102, as shown in FIG. 18B. This extension 108 has threading 110 along the outer wall. The threading 110 of the extension 108 is complementary to the threading 106 of the central recess 104 in the cap 102 so that one PCF bottle 100 may be screwed into the cap 102 of another PCF bottle 100' to form a stack of bottles, as illustrated in FIG. 17. Each bottle is self-contained and individual macromolecule solutions can be provided in each bottle. The stack of PCF bottles fits into one cylinder 101. The stack can be formed with PCF bottles having the same size or may be formed with PCF bottles of different sizes. The stackable PCF bottles may have a variety of volumes including, for example, 1 mL, 5 mL, 10 mL, or 20 mL.

During operation the PCF cap 102 of one PCF bottle 100 is in direct thermal contact with the cold plate 112 of the RIM through the cylinder lid 114. As the temperature of the cold plate is changed a gradient is formed in the first PCF bottle. A gradient is also formed in the other PCF bottles as heat is transferred along the stack of bottles. However, the temperature gradient decreases along the stack, as illustrated in FIG. 17.

This particular arrangement of PCF bottles allows for the testing of more samples and more crystallization conditions in the same volume as the embodiment of the crystallization device depicted in FIGS. 1–10. In particular, the same sample may be tested using different gradient values by providing the same sample in all of the PCF bottles in the stack.

Figure 19:
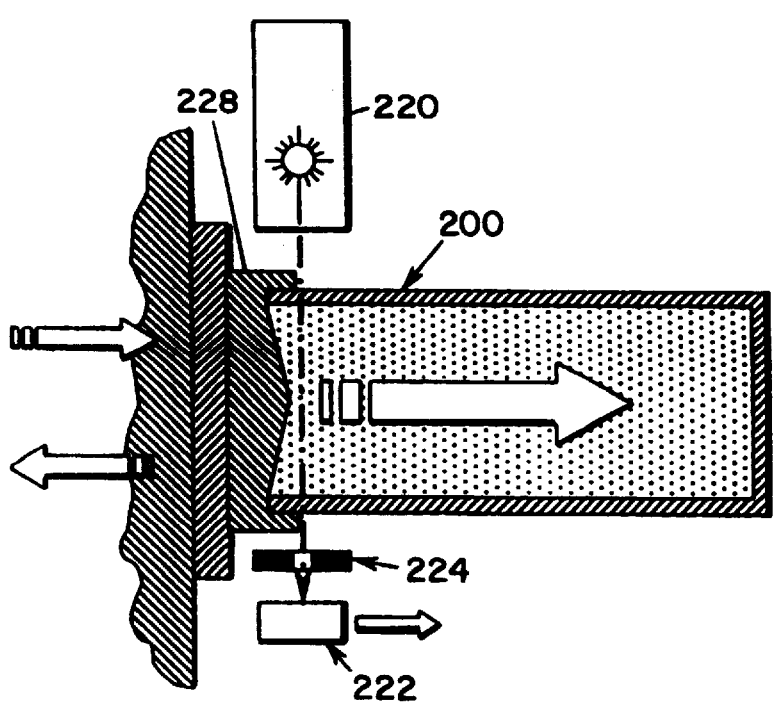
FIG. 19 is a cross-sectional view of a PCF with a light scattering measurement device, according to the invention.
Figure 20:
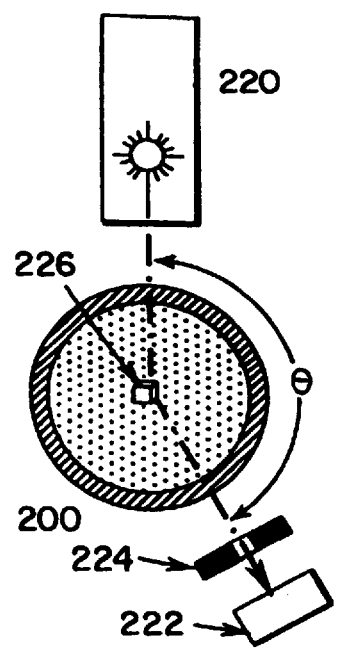
FIG. 20 is a transverse cross-sectional view of the PCF of FIG. 19.

Another embodiment of the invention includes a light scattering apparatus for determining the onset of the production of crystals, as shown in FIGS. 19 and 20. The light scattering apparatus includes a light source 220, a detector 222, and an optional aperture 224 which are arranged around the PCF bottle 200. The light source 220 may be a monochromatic source, such as a laser, or a polychromatic source, such as a lamp. Typically, the light source will generate light of a particular frequency or with a narrow frequency bandwidth. A filter can be used with a polychromatic light source to provide light with a narrow frequency bandwidth. A variety of detectors 222 may be used, including, for example, a monochromator or photodiode. An optional aperture 224 may be used to limit the region from which scattered light can be received.

Typically, the light source 220 and detector 222 can not be directly placed within the canister. Instead, light may be directed through apertures in the canister, either directly or through the use of optical equipment, such as mirrors. In other cases, light may be directed through optical waveguides, including, for example, optical fibers, into and out of the canister. These methods for directing the light from light source 220 to the sample and the scattered light to the detector 222 may be used individually or in combination.

Typically, an angle, θ, between the light source 220 and the detector 222 will be chosen so that light, which is refracted by the PCF bottle 200 and the solution in the bottle, will not substantially illuminate in the detector in the absence of a crystal 226. However, once a crystal or crystal nucleus has formed then the light may be scattered into the detector and provide a signal, such as an increased detector voltage. It is believed that angles between the light source 220 and detector 222 ranging from about 90° to 165° are particularly useful. However, any angle between 0° and 180° may be used depending on the optical properties of the materials through which the light travels.

The light source 220 and detector 222 are preferably aligned so that light passes just below the V-shaped portion of the PCF cap 228. Although no theory is necessary to the invention, it is believed that nucleation begins in the vicinity of the PCF cap 228.

A user or computer observing the data from the detector 222 can determine the onset of nucleation and adjust the temperature ramp accordingly. One example illustrating the alteration of the temperature ramp based on light scattering data is provided in Example 3 in which, when nucleation was detected, the temperature ramp was slowed. The data from the detector 222 may also be sent to a computer for recording. In some embodiments, the temperature ramp may be altered by the computer when crystals or crystal nuclei are detected. This may occur, for example, when a particular threshold value of the detector signal is achieved or when a threshold is met over a predetermined time interval or when a threshold is exceeded a predetermined number of times.

Biological macromolecules for which crystals are producible in accordance with the present invention are those naturally occurring or genetically engineered organic compounds having molecular weights of at least about 1000. Exemplary biological macromolecules include proteins, nucleic acids, proteoglycans, protein-lipid complexes, and glycoproteins. Precipitating (crystallizing) agents are those compounds that, when added to the solution of the biological macromolecule, cause the solution to become supersaturated, leading to protein-protein aggregation resulting in the formation of protein crystals. Exemplary precipitating agents include polyethylene glycol (PEG), 2-methyl-2,4-pentanediol (MPD), ammonium sulfate, and sodium chloride. The particular agent needed for a particular biological macromolecule will be readily apparent to the skilled artisan, as demonstrated in Scopes, *Protein Purification, Principles and Practice*, second edition, Springer, Verlag, 1987, New York, pp. 298–299, Blundell, et al., *Protein Crystallography*, Academic Press, 1976, New York, pp. 59–82, and McPherson, *Preparation and Analysis of Protein Crystals*, John Wiley & Sons, 1982, New York, pp. 102–108, the disclosures of which are incorporated herein by reference.

In accordance with the method of the present invention, temperature change is used to effect crystal growth of the biological macromolecules. Both a warm-to-cold gradient and a cold-to-warm gradient can be used depending on the biological macromolecule that is to be crystallized. Temperature change is used to control crystal growth because it is noninvasive, i.e., the pH, the protein concentration, and the precipitating agent concentration do not have to be changed. Also, no seeding is involved.

Problems encountered on earth in using temperature change to grow crystals are minimized in a microgravity environment. On earth, temperature gradients can set up large convection currents, which can distort and adversely affect protein crystal growth. In a microgravity environment, temperature gradients do not cause such convection currents because of the minimal gravitational force exerted.

Temperature gradients in both directions are effective in growing protein crystals in accordance with the present invention. The temperature gradient necessary for crystallization depends upon the biological macromolecule used. Insulin and catalase, for example, crystallize by reducing the temperature of a heated solution to create a temperature gradient therein. This happens because the protein is more soluble at warmer temperatures, and as it is cooled, it crystallizes out of solution. Other proteins that are known to crystallize using temperature decrease to effect a temperature gradient can also be crystallized in accordance with the present invention.

On the other hand, affecting temperature gradients by increasing the temperature can also be used in accordance with the present invention. For example, in Jakoby, "Crystallization as a purification technique," *Methods in Enzymology*, Vol 11, pp. 248–252, Academic Press New York (1971), and Jakoby, *Analytical Biochemistry*, 26, 295–298 (1968), protein crystallization is realized as the temperature is raised from 4° C. to 22° C. This depends on the differential solubility of proteins in a high salt solution as temperature increases. With this procedure, the protein of interest is dissolved at a relatively low concentration in a high concentration of ammonium sulfate at 4° C. The temperature is raised and the protein crystallizes out at the elevated temperature. The increase in temperature increases the activity of the salt which, in turn, increases its effective concentration. This causes more interaction between the salt and the water which essentially ties up large numbers of water molecules. The effective concentration of the water thereby decreases and concomitantly the concentration of the protein increases and it crystallizes out of the solution. Examples of such proteins are alkaline phosphatase and aldehyde dehydrogenase. Other proteins known to crystallize using an increase in temperature to effect a temperature gradient can also be crystallized in accordance with the present invention.

Temperature change, and particularly temperature ramping, is the easiest way to dynamically control the system. Temperature change is noninvasive, readily engineered, and can be modeled with ground-based work. For these reasons, temperature change is an effective regulator of bulk protein crystal growth in microgravity.

In accordance with the present invention, temperature change can be effected by either manually adjusting temperature controls at given time intervals or by using computer control to establish a constant temperature change over time. Preferably, such temperature change should occur at a rate of about 0.0002–0.03° C. per minute, more preferably about 0.003–0.0125° C. per minute, to effect the proper temperature gradient. Ordinarily, a change of about 18° C. in one hour gives only fair crystals, a change of about 18° C. over about 24 hours gives good crystals, and a change of about 18° C. over less than about 6 weeks is necessary to avoid degradation of the crystals. Solution conditions necessary for crystallization, such as the presence of a precipitating (crystallizing) agent or other solution additives; the concentration of biological macromolecule, precipitating agent, and other additives in solution; solution pH; etc., depend on the particular biological macromolecule to be crystallized and will be readily apparent to the skilled artisan.

In accordance with the method and apparatus of the present invention, formation of varying amounts of crystals are possible. Preferably, crystallization conditions are adjusted in accordance with the present invention to produce commercial scale quantities, i.e., at least 0.05 mg, 0.5 mg, 1.0 mg, 500 mg, or 1000 mg of crystals, including gram quantities and kilogram quantities. Preferably, solution volumes of at least 1 mL, more preferably at least 5 mL, and most preferably at least 10 mL, and concentration levels of biological macromolecule of at least 0.2 mg/mL or at least 5 mg/mL are contemplated. Particular conditions necessary to effect these amounts depend on the biological macromolecule to be crystallized, and will be readily apparent to skilled artisans.

The above-described device and method can be used to produce crystals of macromolecules in microgravity which may have one or more superior attributes when compared to earth-grown crystals. A number of advantages are available with the use of microgravity-grown crystals. For example, the macromolecule may be purified by crystallization in a microgravity environment. Recrystallization is a common method for purifying many molecules. In addition, it may be possible to produce larger crystals or crystals with more internal order to enhance the determination of structure by techniques, such as X-ray crystallography. In some cases, crystallization in microgravity may be the singular method to obtain crystals of sufficient size for structure determination. Furthermore, the use of crystalline forms of a macromolecule may enhance some therapeutic applications of the macromolecule. For example, crystalline forms of therapeutic agents have been used as the basis for time-release medication, in which the crystal dissolves over a period of time to provide a desired level of medication.

Microgravity conditions allow the crystals produced in accordance with the present invention to exhibit more order than their earth-grown counterparts. That is, the microgravity-grown crystal produces a higher Bragg angle at its diffraction limit (i.e., the limit of statistically usable data) as compared to earth-grown crystals and/or the microgravity-grown crystals display less thermal vibration of atomic and molecular lattice misorientation as reflected by the positive B slope displayed on a relative Wilson plot when compared to earth-grown crystals of the same biological macromolecule. The Bragg angle and Wilson plot are well known bases for determining the relative order in crystals. DeLucas, et al., *Science,* 246, 651–654 (1989), the disclosure of which is incorporated herein by reference. In X-ray diffraction analysis of crystals, the Bragg angle is the angle at which X-ray diffraction data is generated, which is used to calculate $1/d^2$ $Å^{-2}$ where d is the calculated distance between planes in the crystal, according to the equation $1/d^2 = 4 \sin\beta/\lambda^2$, where $\lambda$ is typically the wavelength equal to 1.5418 Å. For example, at their diffraction limit, $1/d^2$ for crystals for gamma-interferon is 0.11 and for earth-grown crystals is 0.09. The $1/d^2$ values correspond to a limit of resolution for the microgravity-grown crystals of 3.0 Å, and for the earth grown crystals of 3.3 Å. This means that one can decipher molecular detail as small as 3.0 Å in the microgravity-grown crystals, while the smallest molecular detail decipherable in the earth-grown crystals is 3.5 Å. For crystals of porcine elastase, $1/d^2$ is 0.41 and the resolution limit 1.56 Å for microgravity-grown crystals and $1/d^2$ is 0.32 and the resolution limit 1.76 Å for earth-grown crystals. For crystals of isocitrate lyase, $1/d^2$ is 0.19 and the resolution limit 2.3 Å for microgravity-grown crystals, and $1/d^2$ is 0.13 and the resolution limit 2.8 Å for earth-grown crystals. Values are taken from the relative Wilson plot of particular crystals to calculate the crystal disorder produced either by thermal vibration or molecular misorientations. The value B reflects thermal vibration, atomic and molecular lattice misorientations and is calculated from the slope of a relative Wilson plot according to the formula Slope=$\Delta B/2$, where B is the difference between the B value of the earth-grown crystals and microgravity-grown crystals, with a positive $\Delta B$ indicating lower thermal vibration for the microgravity-grown crystals. For gamma interferon, $\Delta B$ is 5 units, where the units are $Å^2$ between the resolution range of 6.0 and 3.65 Å. The absolute value of the B factor for most crystals is between 10 and 20 units. In the resolution range of 3.65–2.9 Å, $\Delta B$ is 18.5 units. For porcine elastase, $\Delta B$ is 5.2 units in the resolution range of 2–1.7 Å. For isocitrate lyase, $\Delta B$ is 6.2 units in the resolution range of 5–2.5 Å.

EXAMPLE 1

An experiment was conducted using the apparatus shown in FIGS. 1–10. Bovine insulin (Sigma, St. Louis, Mo.) having a concentration of 0.4 mg/mL, in a phosphate buffer, was poured into the PCF bottles. At launch plus three hours, the temperature was lowered from 40° C. to 36° C. At launch plus nine hours, the temperature was lowered from 36° C. to 32° C. At launch plus 19 hours, the temperature was lowered from 32° C. to 28° C. At launch plus 26 hours, the temperature was lowered from 28° C. to 22° C.

Figure 11:
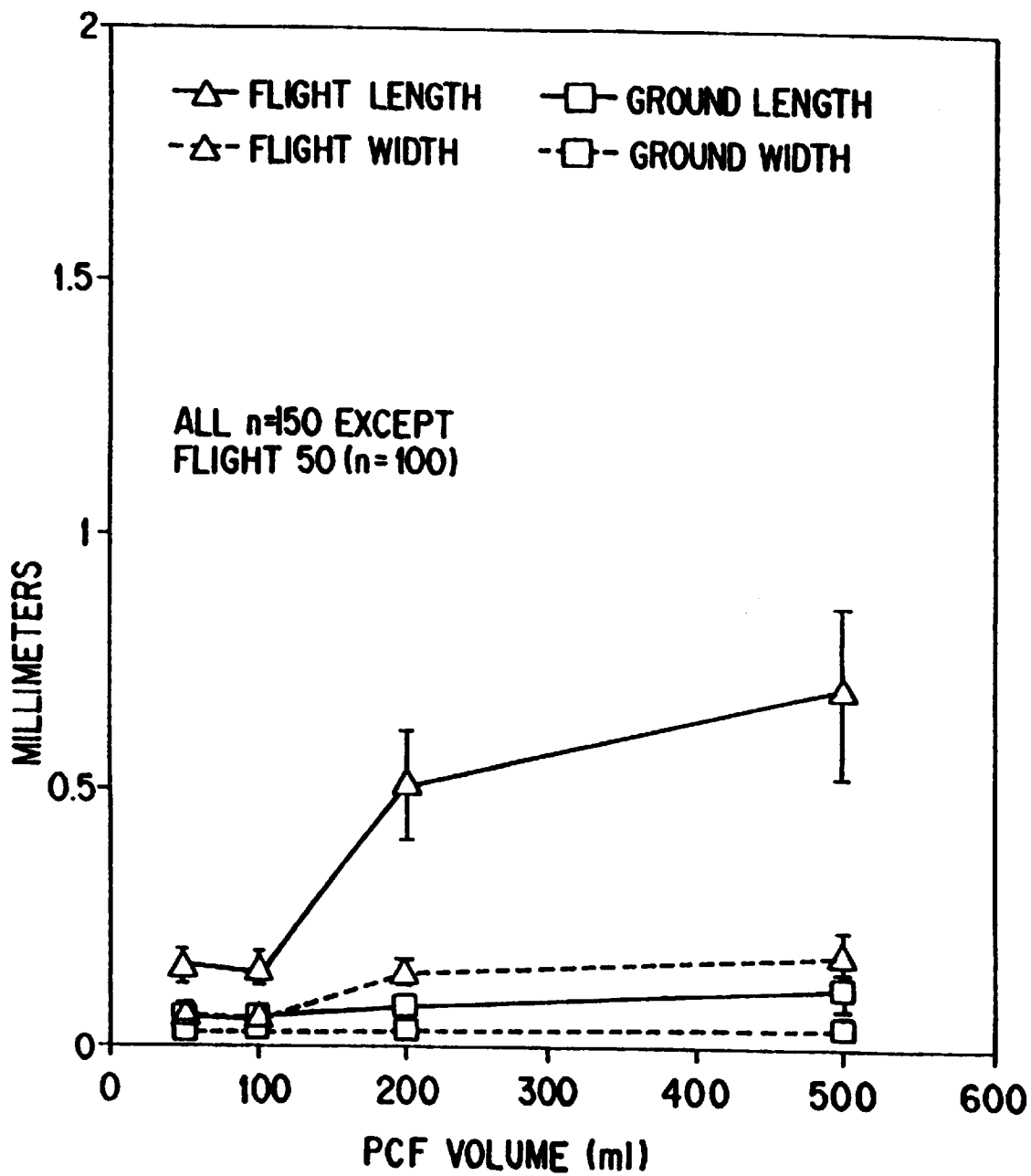
FIG. 11 is a graphical representation of the length and width of free-floating "rosette" crystals in flight and on the ground in one experiment using the present invention.
Figure 13:
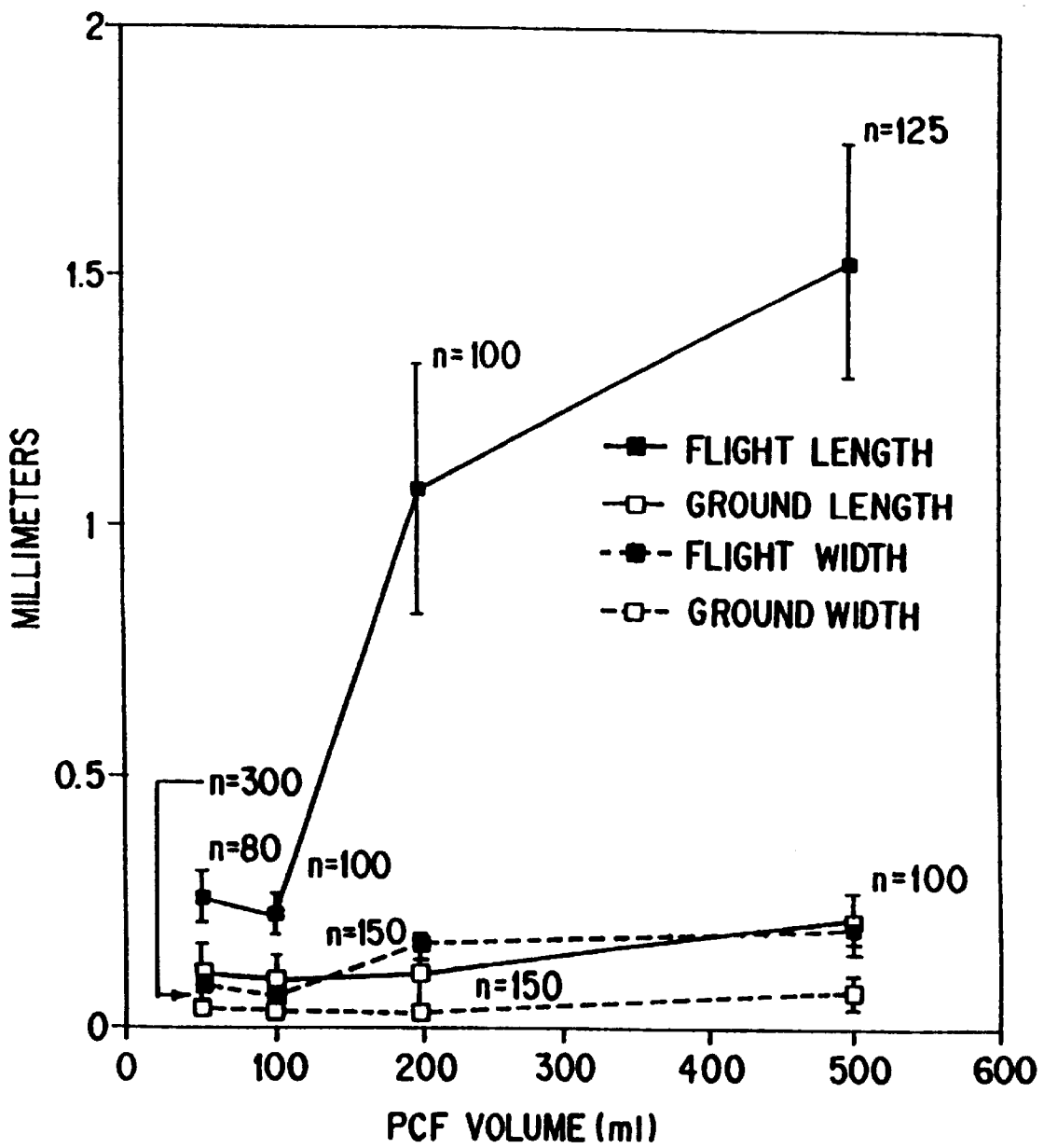
FIG. 13 is a graphical representation of the length and width of free-floating single crystals in flight and on the ground in the experiment of FIG. 11.

The length and width of "rosette" and single crystals grown in flight were measured and compared to the length and width of reference "rosette" and single crystals grown on the ground under otherwise similar conditions. As shown in FIGS. 11 and 13, the free-floating crystals grown in flight were longer and wider than those fact, the ratio of free-floating flight "rosette" crystal size to free-floating ground "rosette" crystal size was found to be:

| PCF | Length | Width |
| --- | --- | --- |
| 500 | 5.94 | 4.13 |
| 200 | 4.71 | 3.43 |
| 100 | 2.40 | 1.74 |
| 50 | 2.76 | 2.34 |

The ration of free-floating flight single crystal size to free-floating ground single crystal size was found to be:

| PCF | Length | Width |
| --- | --- | --- |
| 500 | 10.26 | 3.96 |
| 200 | 8.66 | 3.66 |
| 100 | 2.42 | 1.84 |
| 50 | 2.42 | 2.24 |

Figure 12:
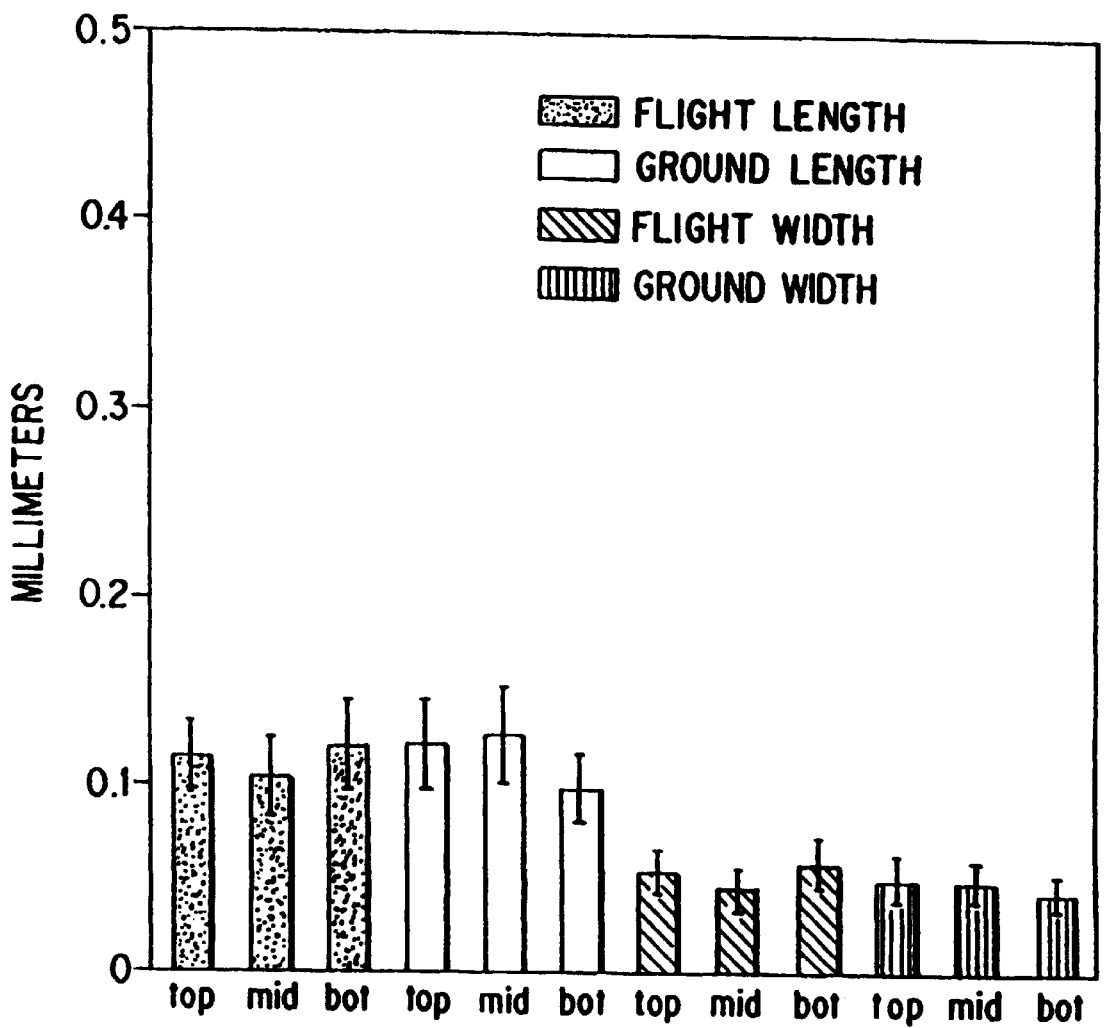
FIG. 12 is a graphical representation of "rosette" crystal size in flight and on the ground on the side of the PCF relative to its location in the experiment of FIG. 11.
Figure 14:
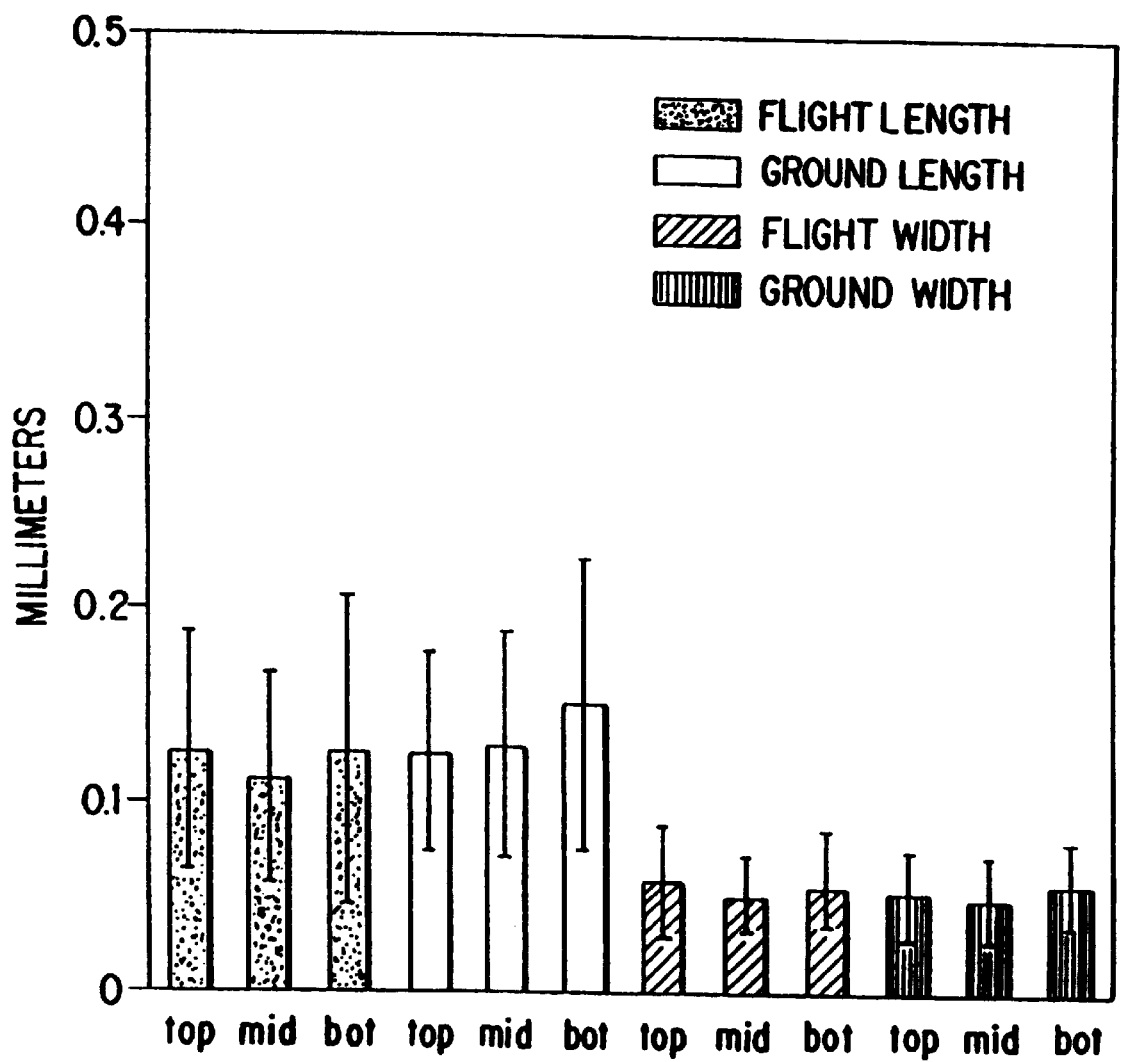
FIG. 14 is a graphical representation of single crystal size in flight and on the ground on the side of the PCF relative to its location in the experiment of FIG. 11.

In addition to the crystals which were found free-floating in the PCF bottles, some crystals were found to be attached to the side of the bottles. As can be seen from FIGS. 12 and 14, there did appear to be a significant difference between the size of the crystals and their location along the longitudinal axis of the PCF bottle. X-ray crystallography indicated that the space grown crystals diffracted to higher resolution

EXAMPLE 2

Another experiment was conducted using the apparatus shown in FIGS. 1–10. Bovine insulin having a concentration of 0.4 mg/mL, in a phosphate buffer, was poured into the PCF bottles. At launch plus four hours., the temperature was lowered from 40° C. to 22° C.

Figure 15:
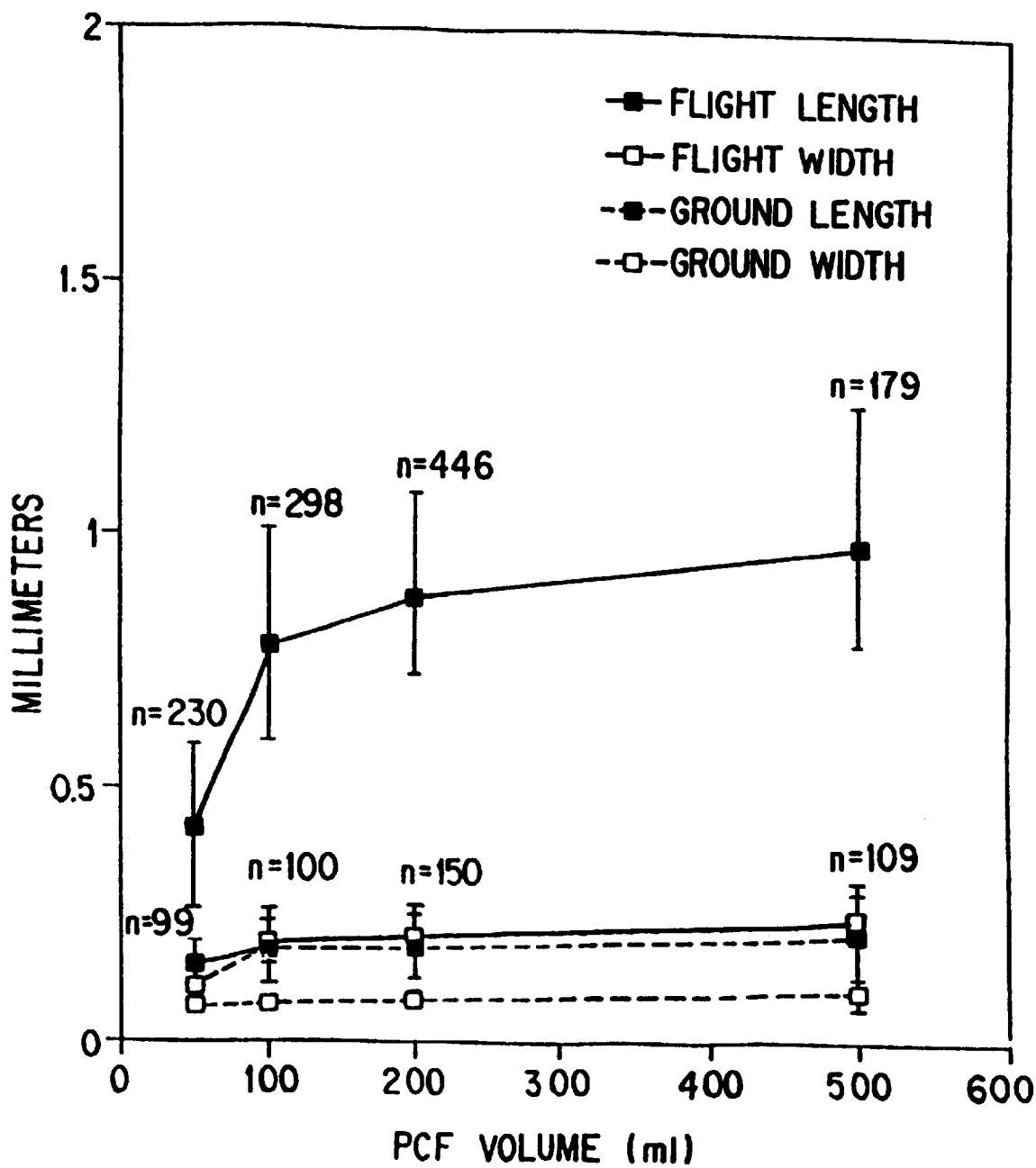
FIG. 15 is a graphical representation of the length and width of free-floating single crystals in flight and on the ground in another experiment using the present invention.

As shown in FIG. 15, the free-floating crystals grown in flight were longer and wider than those grown on the ground. In fact, the ration of free-floating flight single crystal size to free-floating ground single crystal size was found to be:

| PCF | Length | Width |
|-----|--------|-------|
| 500 | 4.58 | 2.55 |
| 200 | 4.65 | 2.64 |
| 100 | 4.12 | 2.68 |
| 50 | 2.76 | 1.65 |

Figure 16:
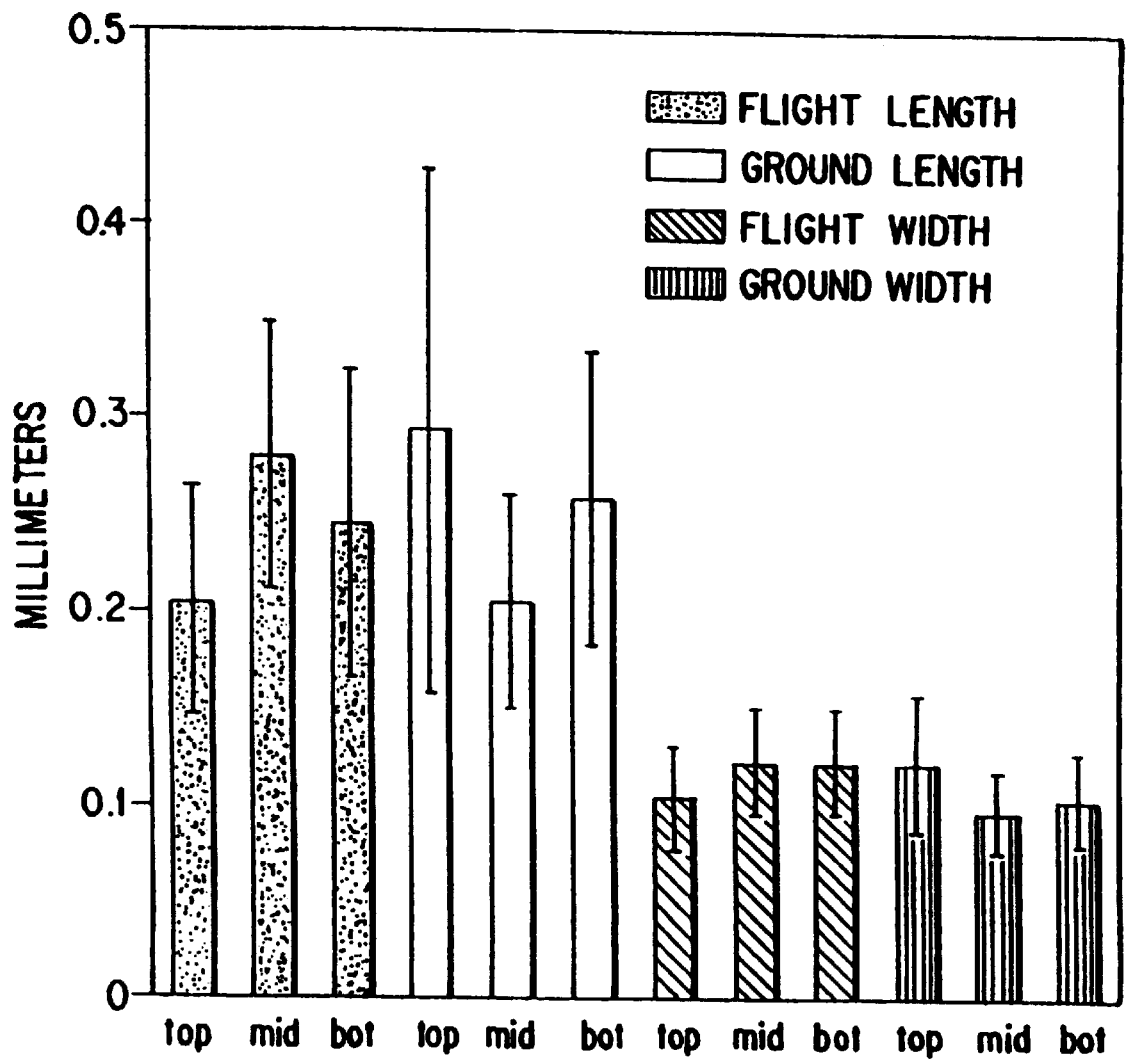
FIG. 16 is a graphical representation of single crystal size in flight and on the ground on the side of the PCF relative to its location in the experiment of FIG. 15.

As can be seen from FIG. 16, again there did not appear to be a significant difference between the size of the crystals attached to the side of the PCF bottle and their location along the longitudinal axis of the PCF bottle. X-ray crystallography indicated that the space grown crystals diffracted to higher resolution than their earth grown controls.

While there are shown and described present embodiments of the invention, it is to be distinctly understood that the invention is not limited thereto, but may be otherwise variously embodied and practiced within the scope of the following claims.

EXAMPLE 3

Four 0.75 g samples of human recombinant insulin (Eli Lilly & Co., Indianapolis, Ind.) red into four separate 500 mL beakers. To each sample, 7.5 mL of 0.15M zinc acetate was added creating a cloudy solution. Next, 37.5 mL of 0.2M sodium citrate wan added and the resulting solution became clear. For two of the solutions, 30 mL of 5% phenol was slowly added to each of the solutions. These solutions were labeled "R6R". For each of the other two solutions, 25 mL of acetone was measured in a graduate cylinder and then 1.25 grams of 4-hydroxybenzamide was added to the acetone. The acetone mixture was then quantitatively added to the insulin solutions followed by 5 mL of water and these latter two solutions were labeled "T3R3-4H".

9 g of NaCl was added to each sample. The pH of each sample was checked immediately after adding the NaCl and the samples were quickly stabilized to a pH of 7.0–7.4. As the solution cleared, the pH of the samples was slowly raised to 9.0–9.8 until all of the samples were clear.

The pH of the samples labeled "R6R" was slowly lowered to 8.5 using 0.75M or 0.37M HCl. The pH of the samples labeled "T3R3-4H" was slowly lowered to 5.7 using 0.75M or 0.37M HCl. Each sample was observed until it began to turn slightly cloudy (approx. 10–30 min.). The samples were divided into about ten 50 mL Corning, modified polystyrene, plug-seal centrifuge tubes labeled "R6R" and "T3R3-4H". The centrifuge tubes were placed in a water bath at 50° C. and incubated for 2 hours. After incubation, 20 mL aliquots were filtered through a 0.22 μm MSI nylon filter (Micro Separations, Inc., available from Fisher Scientific, Atlanta, Ga.) into 50 mL tubes. The aliquots were then combined into two bottles labeled "R6R" and "T3R3-4H", respectively.

The PCF bottles and caps were preincubated at 50° C. A predetermined volume of sample was then measured out for each PCF bottle for both flight and ground testing. Silicon grease was applied to the O-rings of the PCF bottle. The caps and O-rings were carefully placed on the PCF bottle and the caps were screwed onto the PCF bottle by hand. Each PCF bottle was checked for bubbles, which if found were removed. A torque-adapter was then attached to the cap and the cap was torqued to about 15 N m (130 lbs-in). The sealed PCF bottles were then placed in a water bath at 50° C. The PCF bottles were later placed in the aluminum cylinders and introduced into a CRIM prior to the space flight.

The formation of crystals was observed by a light scattering device, as shown in FIGS. 19 and 20. The light source was a 19 mW, 690 nm laser from Power Technology (part no. 902 081200) and the detector was a modified detector from Hamamatsu (part no. HC 220-01). The insulin solutions were allowed to incubate at 40° C. for 8 hours. Then the temperature of the cold plate was decreased from 40° C. to 28° C. by hourly incremental steps over the next 16 hours (approximately 0.75° C./hour), as shown in FIGS. 21–22. The temperature ramp was then slowed so that the temperature was decreased from 28° C. to 22° C. over a period of about 80 hours, as shown in FIGS. 23–24.

The voltage of the detector of the light scattering device is also provided on FIGS. 21–24. For both the "R6R" and "T3R3-4H" samples, the onset of the production of crystals occurs at about 28 ° C. and about 24–28 hours after the experiment has begun.

Figure 25:
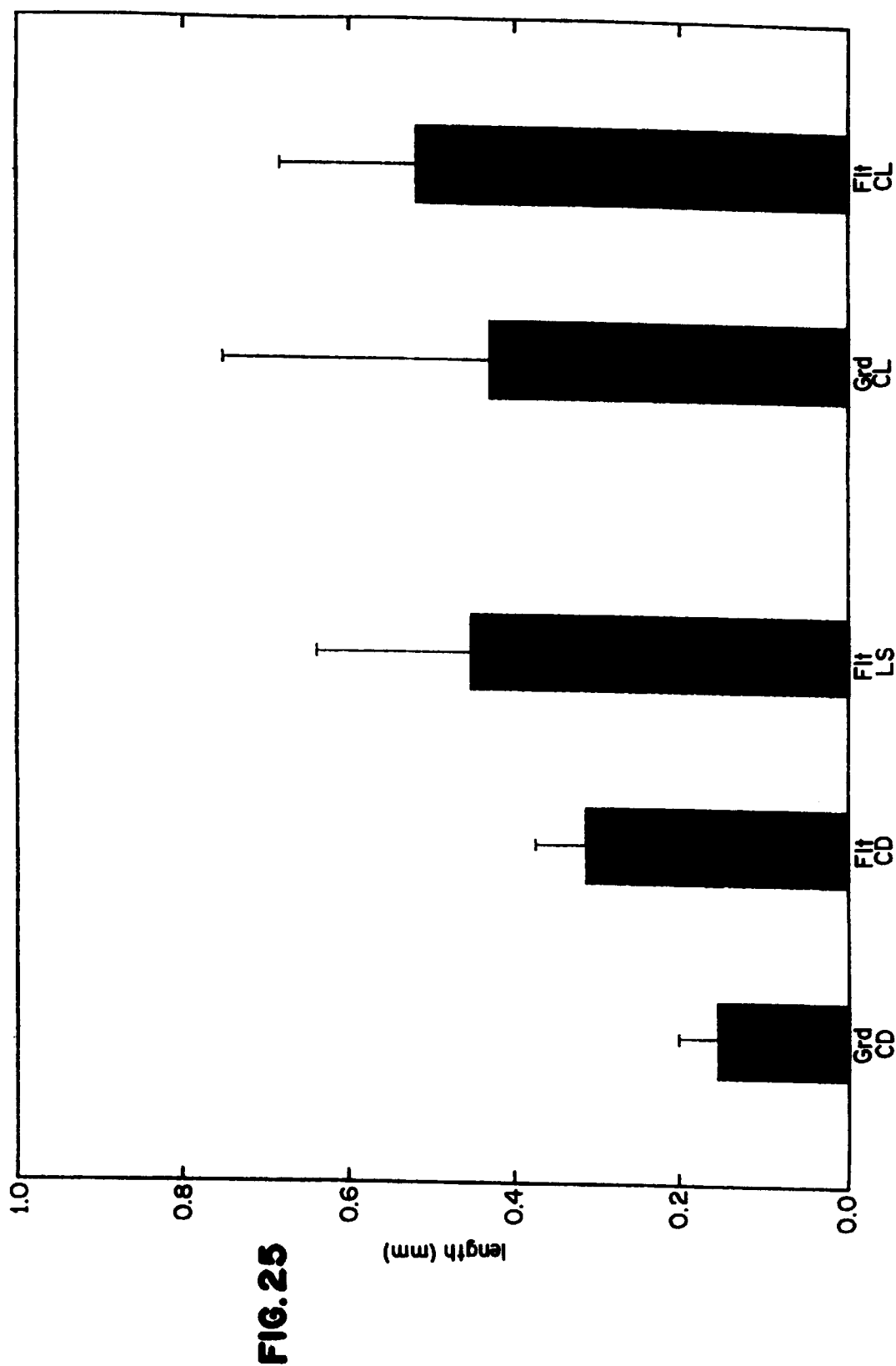
FIG. 25 is a graphical representation of the average crystal lengths for insulin grown on the ground and in flight.
Figure 26:
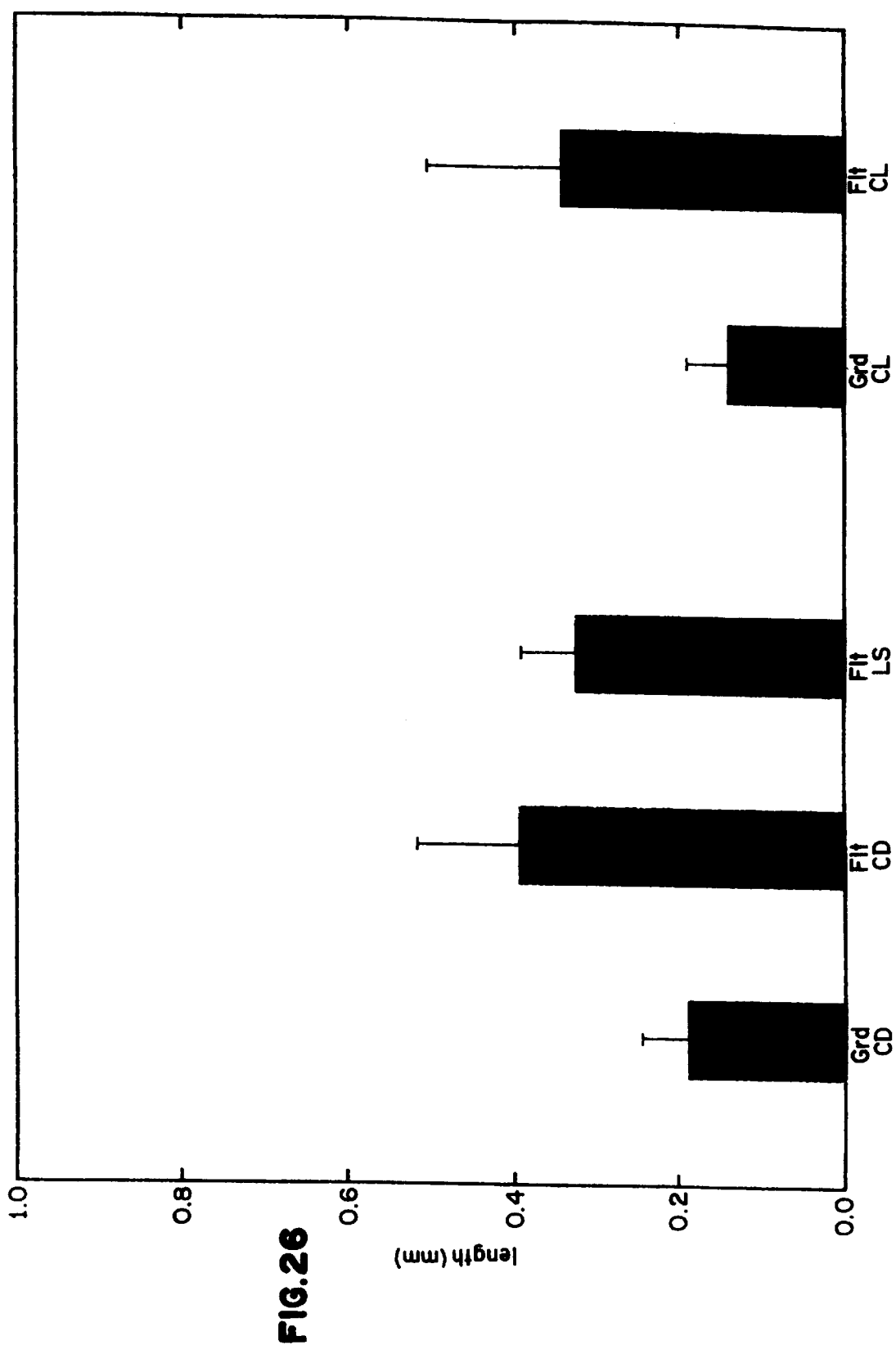
FIG. 26 is a graphical representation of the average crystal lengths for insulin grown on the ground and in flight, in this case, the insulin was bound to hydroxybenzamide.

FIGS. 25 and 26 illustrate the difference in length for both the "R6R" and "T3R3-4H" ground and flight samples. The "R6R" space-grown samples in constant diameter PCF bottles (CD) or using light scattering (LS) were larger than similar earthgrown samples. However, both earth- and space-grown samples prepared in constant length PCF bottles (CL) were larger still, although the space-grown samples were still slightly longer. All of the "T3R3-4H" space-grown samples were longer than the earth-grown comparisons.

Figure 27:
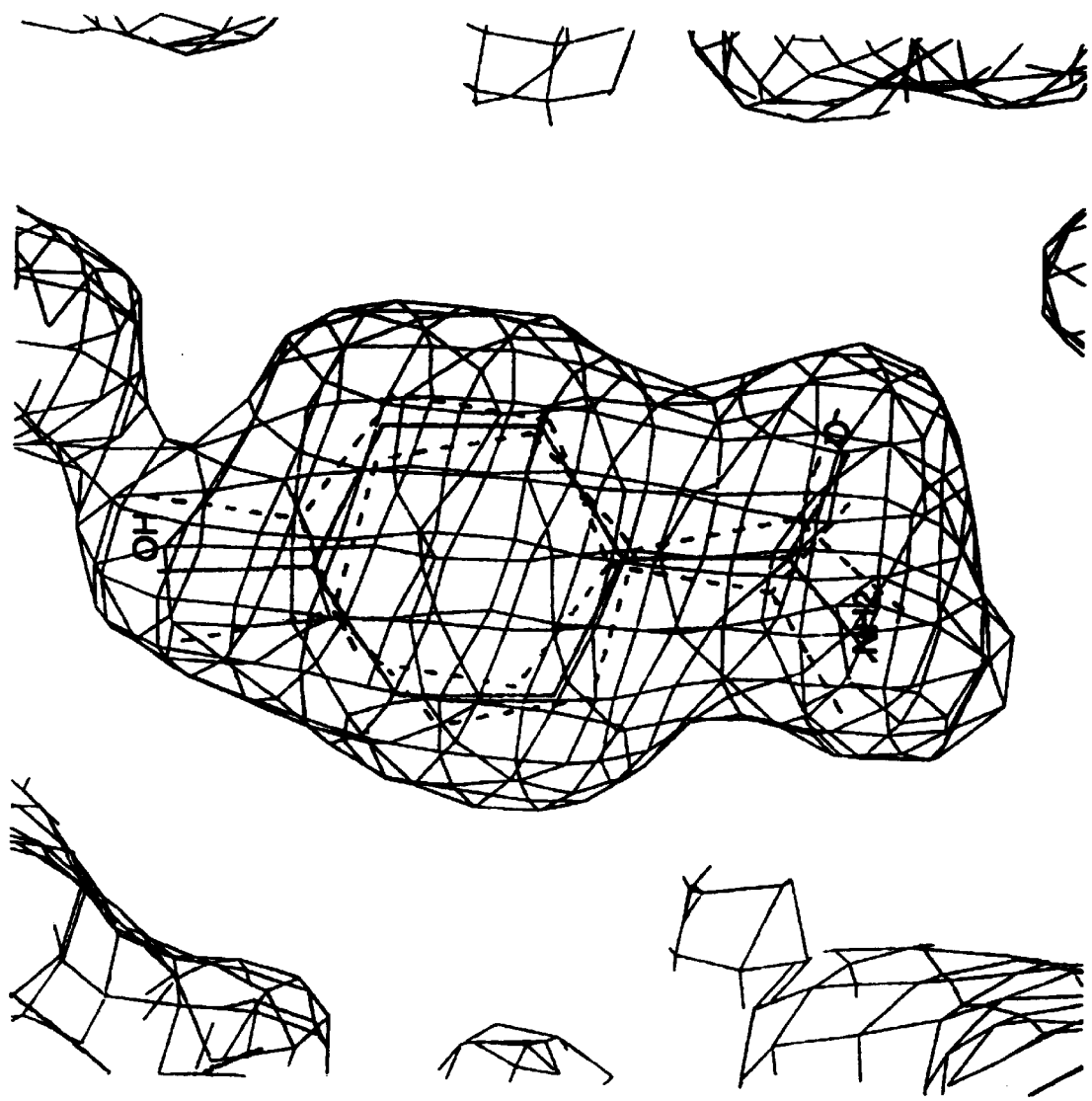
FIG. 27 is an electron density map obtained from X-ray diffraction data of an earth-grown crystal of insulin bound to hydroxybenzamide.
Figure 28:
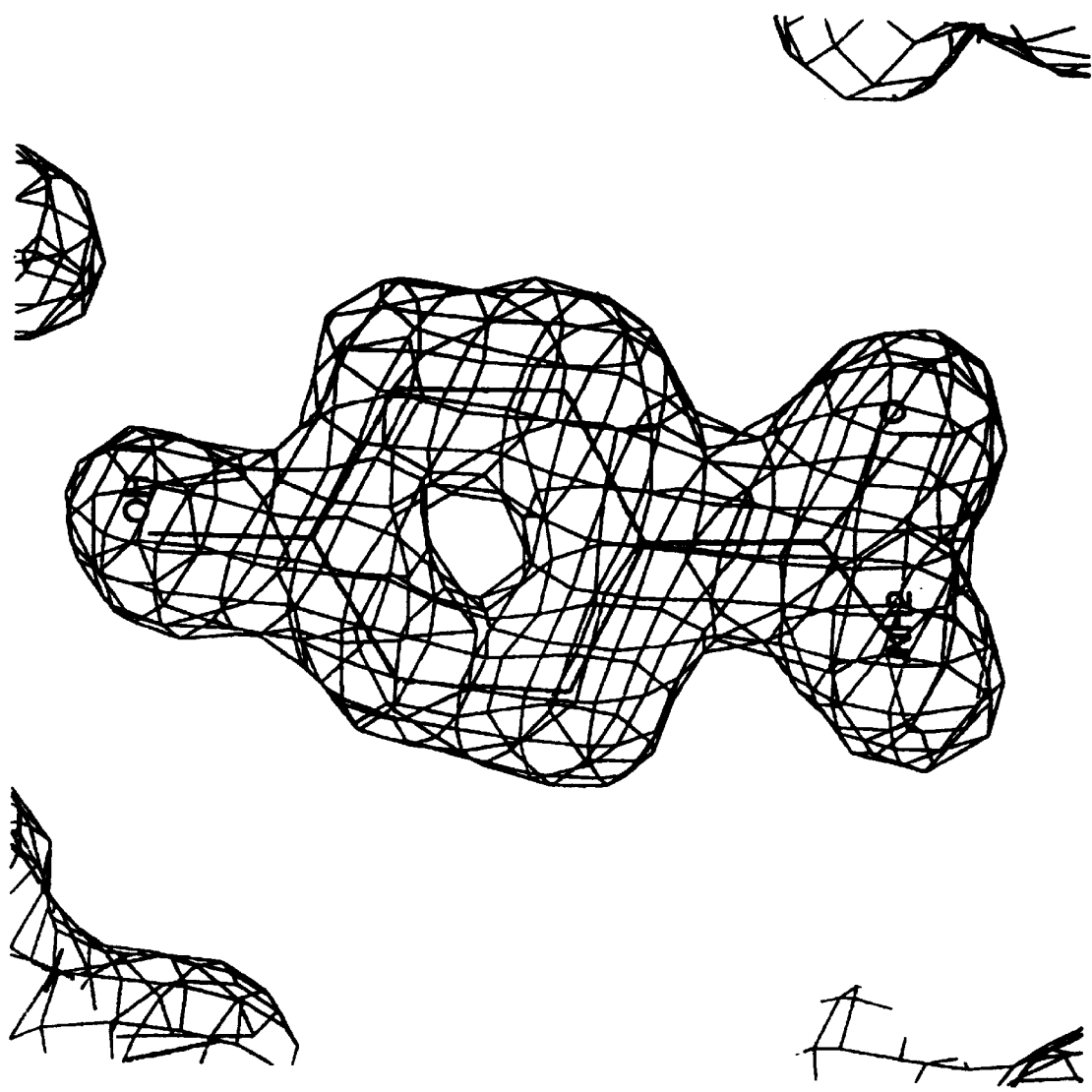
FIG. 28 is an electron density map obtained from X-ray diffraction data of a space-grown crystal of insulin bound to hydroxybenzamide.

FIGS. 27 and 28 provide comparative electron density maps obtained by X-ray diffraction of the hydroxybenzamide substituent added to recombinant human insulin to form the "T3R3-4H" samples. FIG. 27 is from an earth-grown sample and FIG. 28 is from a space-grown crystal. As clearly illustrated in these two figures, the space-grown crystals produce better X-ray diffraction data. The detail from the space-grown crystal is sufficient to determine the central region of the benzene ring.

EXAMPLE 4

Studies were initiated using zinc-interferon solutions (Schering-Plough Research Institute, Kenilworth, N.J.) of 10 mg/mL protein and 20–40 mM sodium acetate at pH 6.0. The ionic strength of the solutions was varied using 0–150 mM sodium acetate/zinc acetate. Below 18 mM sodium acetate, the interferon solutions remained turbid at 4° C. At sodium acetate concentrations above 18 mM, the zinc-interferon solution remained clear at 4° C., but could not support crystal growth upon ramping the temperature to 22° C. Tests were also performed on the ground using linear temperature ramps from 4–22° C. over 12–96 hour time periods.

For the space experiments, the samples were loaded into the PCF bottles and then into a cooled CRIM at 4° C. In microgravity, the temperature was raised from 4° C. to 22° C. over four days.

Upon inspection of the crystals produced in space, it was noted that these crystals remained in suspension in the interferon protein solution. Crystals grown on earth using the same solutions and temperature ramp were coated on the walls of the PCF bottle.

The overall length and width of the space grown crystals was approximately 2.4 times that of the earth grown crystals.

EXAMPLE 5

Crystals of a new recombinant form of human insulin (insulin', a Lys-Pro insulin with the commercial name of Humalog) from Eli Lilly were formed in microgravity. The insulin' samples were provided in stackable PCF bottles: twelve 5 mL bottles and twelve 1 mL bottles, and one 50 mL non-stackable PCF bottle. Four of the 5 mL bottles and four of the 1 mL bottles were coated with bovine albumin (Sigma, St. Louis, Mo.) by incubating the bottles with a 1 mg/mL aqueous solution of bovine albumin for four hours. After the incubation, the bottles were emptied and allowed to air dry for 24 hours. Six of the 5 mL bottles and six of the 1 mL bottles were coated with bovine albumin and Prosil-28. PCF bottles were filled with a 1:100 aqueous dilution of Prosil-28 (Fisher Scientific, Atlanta, Ga.), capped and incubated at room temperature for 5 minutes. The Prosil-28 solution was poured out of the PCF bottle which was allowed to air dry overnight. The PCF bottle was then coated with bovine albumin using the procedure described above.

10 mg/mL and 20 mg/mL solutions of insulin' were prepared. For the 10 mg/mL solutions, 0.357 g of insulin' was placed in a beaker. 179 mL of 0.02M HCl was added to the insulin', followed by 0.428 mL of a 20% zinc chloride solution and then 0.589 mL of 90% phenol. 71 mL of 0.2M sodium citrate was added to the insulin' solution. The insulin' solution was then titrated with 2.5 M HCl to pH 5.9.

For the 20 mg/mL solutions, 0.400 g of insulin' was provided in a beaker. 100 mL of 0.02M HCl was added to the insulin', followed by 0.480 mL of a 20% zinc chloride solution and then 0.330 mL of 90% phenol. 40 mL of 0.2M sodium citrate was added to the insulin' solution and then an amount 1.0M ammonium hydroxide was added so that the pH of the solution was the same as the pH of the 10 mg/mL solution prior to titration by HCl. The insulin' solution was then titrated with 2.5 M HCl to pH 5.9.

Each sample was divided into two separate 200 mL bottles. One bottle of each sample was incubated for 15–30 minutes at 50° C. and the other bottle was incubated for the same period of time at 60° C. The temperature was then ramped down to 44° C. over thirty minutes.

The PCF caps and bottles were preincubated at 44° C. The O-rings for the PCF bottles were coated with silicon grease. Each of the bottles were loaded with solution and the caps were placed onto the bottles with torques of about 15 N m (130 lbs-in) for the 50 mL bottle, about 5 N m (45 lbs-in) for the 5 mL bottles and about 2.5 N m (22–24 lbs in) for the 1 mL bottles. The 1 mL bottles were stacked together and torqued with about 1 N m (9–11 lbs-in). The 5 mL were provided in two stacks with torques of about 1 N m (9–11 lbs-in). The samples were then placed in the CRIM. In microgravity, the temperature was decreased from 40° C. to 22° C. over four days.

Upon investigation of the samples, it was found that crystals had formed in the solution. The lower protein concentration (10 mg/mL) provided larger crystals. There was no difference for samples incubated at the two different temperatures (50° C. and 60° C.). The crystals in the 5 mL PCF bottles were indistinguishable from those in the 1 mL PCF bottles, but those in the 50 mL container were larger. In addition, the siliclad/albumin and albumin coatings did not minimize crystal formation on the polysulfone surface of the PCF bottles. The length and width of space-grown crystals was 1.4–1.6 times that of earth-grown crystals and the volume of space-grown crystals was 3.5 times that of their earth-grown counterparts.

EXAMPLE 6

Crystals of a new recombinant form of human insulin (insulin', Lys-Pro insulin available under the commercial name of Humalog) from Eli Lilly and standard human recombinant insulin were produced in microgravity. Several different solutions of insulin' were used. The first solution included 138 mg of insulin' measured out into a beaker. 69 mL of 0.02 M HCl was added, followed by 0.165 mL of 20% zinc chloride, 0.255 mL of 90% phenol, 7 mL of 0.2M sodium citrate, 14 mL of water, and 2.630 g of sodium chloride. At each addition, the pH of the solution was measured. The solution was then titrated with $NH_4OH$ to clear and then back titrated with HCl to pH 5.62. 44 mL of the sample was removed and marked as sample #1. The remainder was titrated with HCl to pH 5.52 and marked as sample #2. Both samples were incubated in a water bath at 55° C. until the sample cleared and then placed into a second water bath at 47° C. prior to loading into PCF bottles and aluminum cylinders. The total time in the water baths was approximately 4–8 hours.

The second solution included 138 mg of insulin' measured out into a beaker. 69 mL of 0.02 M HCl was added, followed by 0.165 mL of 20% zinc chloride, 0.255 mL of 90% phenol, 21 mL of 0.2M sodium citrate, and 2.630 g of sodium chloride. At each addition, the pH of the solution was measured. The solution was then titrated with HCl to pH 5.52. 44 mL of the sample was removed and marked as sample #3. The remainder was titrated with HCl to pH 5.62 and marked as sample #4. Both samples were incubated in a water bath at 55° C. until the sample cleared and then placed into a second water bath at 47° C. prior to loading into PCF bottles and aluminum cylinders. The total time in the water baths was approximately 4–8 hours.

The third solution included 138 mg of insulin' measured out into a beaker. 69 mL of 0.02 M HCl was added, followed by 0.165 mL of 20% zinc chloride, 0.255 mL of 90% phenol, 21 mL of 0.2M sodium citrate, and 2.630 g of sodium chloride. At each addition, the pH of the solution was measured. The solution was then titrated with HCl to pH 5.62. 44 mL of the sample was removed and marked as sample #5. The remainder was titrated with HCl to pH 5.52 and marked as sample #6. Both samples were incubated in a water bath at 55° C. until the sample cleared and then placed into a second water bath at 47° C. prior to loading into PCF bottles and aluminum cylinders. The total time in the water baths was approximately 4–8 hours.

The fourth solution included 356 mg of insulin' measured out into a beaker. 178 mL of 0.02 M HCl was added, followed by 0.427 mL of 20% zinc chloride, 0.587 mL of 90% phenol, and 71 mL of 0.2M sodium citrate. At each addition, the pH of the solution was measured. The solution was then titrated with HCl to pH 5.9. 44 mL of the sample was removed and marked as sample #7. The remainder was titrated with HCl to pH 5.8 and a 44 mL and 55 mL samples were removed and marked as sample #8 and #8' respectively. The rest was titrated with HCl to pH 5.7 and marked as sample #9. All of the samples were incubated in a water bath at 55° C. until the sample cleared and then placed into a second water bath at 47° C. prior to loading into PCF bottles and aluminum cylinders. The total time in the water baths was approximately 4–8 hours.

The fifth solution included 700 mg of human recombinant insulin measured out into a beaker. 70 mL of 0.02 M HCl was added, followed by 7 mL of 0.15 M zinc acetate and 28 mL of 5% resorcinol, 35 mL of 0.2M sodium citrate, and 8.40 g of sodium chloride. At each addition, the pH of the solution was measured. The solution was titrated with NaOH to clear. The solution was then titrated with HCl to pH 6.9. 44 mL of the sample was removed and marked as sample #10. The remainder was titrated with HCl to pH 6.8 and a 44 mL sample was removed and marked as sample #11. The rest was titrated with HCl to pH 6.7 and marked as sample #12. All of the samples were incubated in a water bath at 55° C. until the sample cleared and then placed into a second water bath at 47° C. prior to loading into PCF bottles and aluminum cylinders. The total time in the water baths was approximately 4–8 hours.

All of the samples were independently filtered into 50 mL tubes via 20 mL aliquots per 0.22 $\mu$m MSI nylon filter (Micro Separations, Inc., available from Fisher Scientific, Atlanta, Ga.). Silicon grease was applies to all O-rings for the PCF bottles. The samples were placed in PCF bottles. Sample 8' was placed in a 50 mL PCF bottle, the rest of the samples were placed in 10 mL stackable PCF bottles.

The cap and O-ring were carefully screwed on the PCF bottles to a torque of 15 N m (130 lbs-in) for the 50 mL PCF bottle and 5.5 N m (50 lbs-in) for the 10 mL PCF bottle. Each PCF bottles was placed in a water bath at 47° C.

The 20 mL PCF bottles were stacked together using a torque of about 1.4 N m (12 lbs-in). The filled bottles were kept at 40° C. In microgravity, the temperature was decreased from 40° C. to 22° C. over 24 hours.

Samples #1–6 were prepared with appropriate components to form monoclinic insulin' crystals. Samples #7–9 and #8' were prepared with appropriate components to form rhombohedral insulin' crystals. Samples #10–12 were prepared using insulin and a chelator, resorcinol. For each of the three general types of samples, different pH values were tested to provide information regarding the pH dependence of crystal formation.

Free floating and adherent crystals were observed for each of the three types of samples. The greatest yields were for the rhombohedral insulin' crystals and the insulin crystals. Free floating space-grown monoclinic insulin' crystals were longer and wider than the earthgrown controls. The longest length of the earth-grown crystals was 0.7 mm while the longest length for the space-grown crystal was 2.4 mm.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An apparatus for producing crystals of a macromolecule in microgravity, the apparatus comprising:
   a container having an open end and comprising a material having a low thermal conductivity;
   a thermally conductive lid fitted on the open end of the container to close the container; and
   a heat source/sink suitable for thermal contact with the thermally conductive lid to generate a temperature gradient within the container, wherein a plurality of similar containers with lids are formed into a stack with at least one of the lids in thermal contact with the heat source/sink.

2. The apparatus of claim 1, wherein at least one of the similar containers has a different volume.

3. The apparatus of claim 1, wherein the container has a closed end and an extension protruding from the closed end of the container, the closed end being opposite the open end of the container, and the thermally conductive lid has a recess configured for receiving the extension, the container being adapted for stacking with one or more similar containers by introducing the extension of the container into the recess in the thermally conductive lid of one of the similar containers.

4. The apparatus of claim 1, wherein, when the lid of one container in the stack of containers is in direct thermal contact with the heat source/sink, a different temperature gradient is generated in each container in the stack.

5. The apparatus of claim 1, wherein the apparatus comprises one or more temperature measurement devices provided on the container for determining the temperature of a solution in the container.

6. The apparatus of claim 5, wherein at least two temperature measurement devices are provided on the container for determining the temperature gradient in the solution.

7. The apparatus of claim 1, wherein the apparatus further comprises a light source and a detector, the light source and detector being aligned around the container so that light from the light source that is scattered by a crystal or crystal nucleus in a solution in the container is detected the detector.

8. The apparatus of claim 7, wherein the light source and detector are aligned around the container so that light from the light source which is not scattered by a crystal in the solution is not detected by the detector.

9. The apparatus of claim 8, wherein the light source and the detector are aligned around the container so as to define an angle with a center of the container that ranges from about 90° to 165°.

10. The apparatus of claim 7, wherein the light source and detector are aligned around the container so that light from the light source passes through a portion of the solution near the thermally conductive cap.

* * * * *